US009486394B2

(12) United States Patent
Abram et al.

(10) Patent No.: US 9,486,394 B2
(45) Date of Patent: *Nov. 8, 2016

(54) PHARMACEUTICAL FOAM

(71) Applicant: STIEFEL WEST COAST, LLC, Wilmington, New Castle, DE (US)

(72) Inventors: Albert Zorko Abram, Wantirna (AU); Lilian Fuchshuber, Narre Warren (AU)

(73) Assignee: STIEFEL WEST COAST, LLC, Wilmington, DE (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/053,085

(22) Filed: Oct. 14, 2013

(65) Prior Publication Data
US 2014/0042051 A1 Feb. 13, 2014

Related U.S. Application Data

(60) Continuation of application No. 13/307,533, filed on Nov. 30, 2011, now Pat. No. 8,586,008, which is a continuation of application No. 12/783,824, filed on May 20, 2010, now abandoned, which is a
(Continued)

(51) Int. Cl.
*A61K 9/12* (2006.01)
*A61K 31/74* (2006.01)
(Continued)

(52) U.S. Cl.
CPC ............... *A61K 8/046* (2013.01); *A61K 8/38* (2013.01); *A61K 8/671* (2013.01); *A61K 9/12* (2013.01);
(Continued)

(58) Field of Classification Search
CPC .. A61K 8/046; A61K 31/4025; A61K 45/06; A61Q 19/00
See application file for complete search history.

(56) References Cited

U.S. PATENT DOCUMENTS 4,806,262 A 2/1989 Snyder
4,882,182 A 11/1989 Halls et al.
(Continued)

FOREIGN PATENT DOCUMENTS

AR 042906 A1 7/2005
EP 0 331 489 A2 9/1989
(Continued)

OTHER PUBLICATIONS

Abram, et al., "Mousses", Ch. 19, Jun. 2001, pp. 221-232, Soltec Research Pty Ltd., Rowville, Victoria, Australia.
(Continued)

*Primary Examiner* — Mina Haghighatian
(74) *Attorney, Agent, or Firm* — Nath, Goldberg & Meyer; Joshua B. Goldberg; Scott H. Blackman

(57) ABSTRACT

The present invention provides various pharmaceutically active topical delivery compositions. In particular, compositions of the present invention are present in a pressurized container comprising a quick-breaking alcoholic foaming agent, such that when the composition is released, i.e., dispensed, from the pressurized container, a quick-breaking temperature sensitive foam is formed. In addition, the present invention provides various aspects related to such compositions, including methods for modulating a foam characteristic, methods for improving the shelf-life of a pharmaceutically active compound, methods for the percutaneous treatment of various diseases, infections, and illnesses, and methods for evaluating foam characteristics.

20 Claims, 9 Drawing Sheets

Related U.S. Application Data continuation of application No. 11/349,820, filed on Feb. 7, 2006, now Pat. No. 7,749,488, which is a division of application No. 10/763,379, filed on Jan. 23, 2004, now Pat. No. 7,141,237.

(60) Provisional application No. 60/442,280, filed on Jan. 24, 2003, provisional application No. 60/454,832, filed on Mar. 13, 2003.

(51) Int. Cl.

| | | |
|---|---|---|
| A61K 33/40 | (2006.01) | |
| A61P 17/10 | (2006.01) | |
| A61K 8/04 | (2006.01) | |
| A61K 8/38 | (2006.01) | |
| A61K 8/67 | (2006.01) | |
| A61K 31/4025 | (2006.01) | |
| A61K 45/06 | (2006.01) | |
| A61Q 19/00 | (2006.01) | |

(52) U.S. Cl.
CPC ........... *A61K 9/122* (2013.01); *A61K 31/4025* (2013.01); *A61K 45/06* (2013.01); *A61Q 19/00* (2013.01)

(56) References Cited

U.S. PATENT DOCUMENTS

| | | | |
|---|---|---|---|
| 4,915,934 A | 4/1990 | Tomlinson | |
| 4,981,678 A | 1/1991 | Tomlinson | |
| 5,352,437 A | 10/1994 | Nakagawa et al. | |
| 5,397,564 A | 3/1995 | Seki et al. | |
| 5,446,028 A | 8/1995 | Klein et al. | |
| 5,466,446 A | 11/1995 | Stiefel et al. | |
| 5,516,504 A | 5/1996 | Tomlinson | |
| 5,679,324 A | 10/1997 | Lisboa et al. | |
| 5,690,923 A | 11/1997 | DeVringer et al. | |
| 5,776,430 A | 7/1998 | Osborne et al. | |
| 5,783,202 A | 7/1998 | Tomlinson et al. | |
| 5,788,155 A | 8/1998 | Martin et al. | |
| 5,843,881 A | 12/1998 | Dubois et al. | |
| 5,935,554 A | 8/1999 | Tomlinson | |
| 6,013,637 A | 1/2000 | Klein et al. | |
| 6,126,920 A | 10/2000 | Jones et al. | |
| 6,211,250 B1 | 4/2001 | Tomlinson et al. | |
| 6,231,875 B1 | 5/2001 | Sun et al. | |
| 6,267,949 B1 | 7/2001 | Halls | |
| 6,284,234 B1 | 9/2001 | Niemiec et al. | |
| 6,358,541 B1 | 3/2002 | Goodman | |
| 6,383,471 B1 | 5/2002 | Chen et al. | |
| 6,419,913 B1 | 7/2002 | Niemiec et al. | |
| 6,428,772 B1 | 8/2002 | Singh et al. | |
| 6,730,288 B1 | 5/2004 | Abram | |
| 7,115,277 B2 | 10/2006 | Firestone et al. | |
| 7,141,237 B2 | 11/2006 | Abram et al. | |
| 7,326,408 B2 | 2/2008 | Angel et al. | |
| 7,374,747 B2 | 5/2008 | Abram et al. | |
| 7,387,807 B2 | 6/2008 | Callaghan et al. | |
| 7,749,488 B2 | 7/2010 | Abram et al. | |
| 8,158,109 B2 * | 4/2012 | Abram et al. | 424/45 |
| 8,475,770 B2 * | 7/2013 | Abram et al. | 424/45 |
| 8,586,008 B2 * | 11/2013 | Abram et al. | 424/45 |
| 8,758,728 B2 * | 6/2014 | Abram et al. | 424/45 |
| 2003/0113385 A1 | 6/2003 | Schleicher et al. | |
| 2003/0118511 A1 | 6/2003 | Jones et al. | |
| 2004/0043946 A1 | 3/2004 | Popp | |
| 2005/0014729 A1 | 1/2005 | Pulaski | |
| 2005/0031547 A1 | 2/2005 | Tamarkin et al. | |
| 2005/0042173 A1 | 2/2005 | Besse et al. | |
| 2005/0069566 A1 | 3/2005 | Tamarkin et al. | |
| 2005/0074414 A1 | 4/2005 | Tamarkin et al. | |
| 2005/0075407 A1 | 4/2005 | Tamarkin et al. | |
| 2005/0191343 A1 | 9/2005 | Liang | |
| 2005/0197407 A1 | 9/2005 | DiNardo et al. | |
| 2005/0205086 A1 | 9/2005 | Tamarkin et al. | |
| 2005/0232869 A1 | 10/2005 | Tamarkin et al. | |
| 2005/0238597 A1 | 10/2005 | McCook et al. | |
| 2005/0271598 A1 | 12/2005 | Friedman et al. | |
| 2005/0276842 A1 | 12/2005 | Zhang et al. | |
| 2006/0057168 A1 | 3/2006 | Larm et al. | |
| 2006/0193789 A1 | 8/2006 | Tamarkin et al. | |
| 2006/0275218 A1 | 12/2006 | Tamarkin et al. | |
| 2006/0292080 A1 | 12/2006 | Abram et al. | |
| 2007/0110685 A1 | 5/2007 | Auspitz et al. | |
| 2007/0134276 A1 | 6/2007 | Menegatti et al. | |
| 2007/0189977 A1 | 8/2007 | Zhang et al. | |
| 2007/0190043 A1 | 8/2007 | Sych et al. | |
| 2007/0196323 A1 | 8/2007 | Zhang et al. | |
| 2007/0196453 A1 | 8/2007 | Zhang et al. | |
| 2007/0248658 A1 | 10/2007 | Schroeder et al. | |
| 2007/0280891 A1 | 12/2007 | Tamarkin et al. | |
| 2007/0280972 A1 | 12/2007 | Zhang et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0050317 A1 | 2/2008 | Tamarkin et al. | |
| 2008/0063607 A1 | 3/2008 | Tamarkin et al. | |
| 2008/0299220 A1 | 12/2008 | Tamarkin et al. | |

FOREIGN PATENT DOCUMENTS

| | | |
|---|---|---|
| EP | 1 958 613 A1 | 8/2008 |
| FR | 2 677 369 A1 | 12/1992 |
| GB | 1561423 | 2/1980 |
| JP | H3-500287 | 4/1989 |
| JP | 52-71052 A | 10/1993 |
| JP | 85-12049 A | 12/1996 |
| JP | H10-500700 A | 12/1998 |
| JP | 2001-520184 A | 10/2001 |
| JP | 2004-505900 A | 2/2002 |
| JP | 2002-519441 A | 7/2002 |
| WO | 85/01876 A1 | 5/1985 |
| WO | 86/00196 A1 | 1/1986 |
| WO | 88/04896 A1 | 7/1988 |
| WO | 96/27376 A1 | 9/1996 |
| WO | 97/17075 A1 | 5/1997 |
| WO | 99/20250 A1 | 4/1999 |
| WO | 99/53923 A1 | 10/1999 |
| WO | 00/15193 A1 | 3/2000 |
| WO | 03/039559 A1 | 5/2003 |
| WO | 2004/037225 A2 | 5/2004 |
| WO | 2005/011567 A2 | 2/2005 |
| WO | 2006/040644 A2 | 4/2006 |
| WO | 2007/007208 A2 | 1/2007 |
| WO | 2007/077029 A1 | 7/2007 |
| WO | 2007/082864 A2 | 7/2007 |
| WO | 2008/017914 A2 | 2/2008 |
| WO | 2008/057930 A2 | 5/2008 |
| WO | 2008/075207 A2 | 6/2008 |
| WO | 2008/104214 A1 | 9/2008 |
| WO | 2008/104215 A1 | 9/2008 |
| WO | 2008/148968 A1 | 12/2008 |
| WO | 2008/152444 A2 | 12/2008 |
| WO | 2009/029046 A1 | 3/2009 |

OTHER PUBLICATIONS

Woodford, et al., "Bioavailability and activity of topical corticosteroids from a novel drug delivery system, the aerosol quick-break foam", J Pharm Sci. Jan. 1977, pp. 90-103, vol. 60, No. 1.

Office Action dated May 7, 2015 in corresponding Argentinian Patent Application No. 2004 01 00187.

Richter,J.R. et al., "Efficacy of the fixed 1.2% clindamycin phosphate, 0.025% tretinoin gel formulation (Velac®) and a proprietary 0.025% tretinoin gel formulation (Aberela®) in the topical control of facial acne", Journal of the European Academy of Dermatology and Venereology, vol. 11, pp. 227-233, 1998.

Tschen, Eduardo H. et al., "A Combination Benzoyl Peroxide and Clindamycin Topical Gel Compared With Benzoyl Peroxide,

(56) References Cited

OTHER PUBLICATIONS

Clindamycin Phosphate, and Vehicle in the Treatment of Acne Vulgaris", Therapeutics for the Clinician, vol. 67, pp. 165-169, Feb. 2001.
Gennaro, A.R., "Remington: The Science and Practice of Pharmacy", vol. 2, Edition 19, Chapter 95, "Aerosols" by Sciarra, John J., pp. 1676-1692, 1995.
Gennaro, A.R., "Remington Farmacia", Edition 19a, Chapter 95, "Aerosols" by Sciarra, John J., pp. 2561-2581 (1998).
Leyden, J. et al., "The Combination Formulation of Clindamycin 1% plus Benzoyl Peroxide 5% versus 3 Different Formulations of Topical Clindamycin Alone in the Reduction of Propionibacterium acnes", Am. J. Clin. Dermatol., 2 (4), pp. 263-266 (2001).
Office Action dated Jul. 6, 2015, for corresponding Argentina Patent Application No. 2011 01 02768.

\* cited by examiner

FOAM QUALITY SCALE

| Rating | | Description |
|---|---|---|
| 0 | | Full, fine, stable (holds structure or only a very slow, small collapse over 30-60 sec) |
| 1 | | Mostly fine with a couple of coarser bubbles on surface then stable, or fine then slightly coarser over time |
| 2 | | Slightly coarse initially but reasonably stable, or fine (possibly some slight dimples) with a couple of larger bubbles appearing on surface, or a flat but fine and reasonably stable |
| 3 | | Slightly coarse bubbles then growing larger throughout, or very coarse but stable, or fine (possibly with dimples) then many larger bubbles appearing on surface, or fine then quick collapse |
| 4 | | Coarse bubble quickly grows to larger throughout, or fine but rough surface and quickly to large bubbles throughout, or fine with many large bubbles immediately on surface |
| 5 | | Out as large bubbles, or immediate break to large bubbles |

*FIG. 2*

PHARMACEUTICAL FOAM

CROSS REFERENCE TO RELATED APPLICATIONS

This application is a continuation of U.S. application Ser. No. 13/307,533, filed Nov. 30, 2011, which is a continuation of U.S. application Ser. No. 12/783,824, filed May 20, 2010, which is a continuation of U.S. application Ser. No. 11/349,820, filed Feb. 7, 2006, now U.S. Pat. No. 7,749,488, which is a divisional of U.S. application Ser. No. 10/763,379, filed Jan. 23, 2004, now U.S. Pat. No. 7,141,237, which application claims priority to U.S. Provisional Application Nos. 60/442,280, filed Jan. 24, 2003, and 60/454,832, filed Mar. 13, 2003, the teachings all of which are incorporated herein by reference in their entireties for all purposes.

FIELD OF THE INVENTION

The present invention relates to topical delivery of at least one pharmaceutically active compound, especially clindamycin or its pharmaceutically acceptable salt or a prodrug thereof, alone or in combination with another pharmaceutically active compound.

BACKGROUND OF THE INVENTION

There are many challenges in the topical application of pharmaceutically active agents. One major objective is to achieve percutaneous penetration of the active agent to the site of treatment. The composition should also have desirable cosmetic characteristics. Application should be easy, smooth, and should not leave a noticeable residue on the surface of the skin. Moreover, the composition should not cause irritation, discomfort, or inconvenience.

Many antifungal and antibacterial agents are used topically to treat epidermal infections. Some antibiotics, such as tetracycline and clindamycin, are also used to treat acne and other skin diseases that are caused, directly or indirectly, by bacteria. One of the side-effects of systemically administered clindamycin is colitis, which can be dangerous and even fatal. Thus, in treating acne, it is desirable to administer clindamycin topically. Cleocin T®, manufactured by Pharmacia-Upjohn, contains clindamycin phosphate, which is inactive in vitro, but is hydrolyzed in vivo to the antibacterially active clindamycin. Cleocin T® is currently available as a gel, a lotion, and a topical solution, and is used for topical treatment of acne vulgaris.

Lotion and gel topical dosage forms have the disadvantage of extended rub-in and may leave oily residues. The solution form readily runs off the site of application, and therefore it is difficult to apply controlled amounts using the solution form.

The present invention overcomes these disadvantages by providing a composition having at least one pharmaceutically active compound, which is useful for topical administration as described herein, as a foam that is a non-runny, easy to apply, and uses a low residue vehicle. When the foam is applied, body heat causes the foam structure to break down and deposit the active ingredient(s) in the form of a vehicle resembling a solution. The foam composition provides good control of the application of a small amount of product to the desired area.

SUMMARY OF THE INVENTION

The present invention overcomes the disadvantages of the prior art by providing a pharmaceutically active composition, which is useful for topical administration, as a foam that is a non-runny, easy to apply, and uses a low residue vehicle. Surprisingly, the foam compositions of the present invention provide enhanced delivery of an active compound(s) across the skin compared to gel compositions and without the concomitant disadvantages associated with solution formulations (e.g., runniness, difficulty in applying controlled amounts).

As such, in one aspect, the present invention provides a topical delivery composition in a pressurized container comprising:

up to 15% w/w of at least one pharmaceutically active compound, or its pharmaceutically acceptable salt or a prodrug thereof;

from about 83% to about 97.9% w/w of a quick-breaking foaming agent; and from about 2% to about 7% w/w of an aerosol propellant selected from the group consisting of a hydrocarbon, a chlorofluorocarbon, dimethyl ether, hydrofluorocarbons and a mixture thereof, wherein the composition is a quick-breaking temperature sensitive foam after release from the container.

In one embodiment, the quick-breaking foaming agent comprises a $C_1$-$C_6$ alcohol and water. In a preferred embodiment, the quick-breaking foaming agent comprises a $C_1$-$C_6$ alcohol, a $C_{14}$-$C_{22}$ alcohol, water, and a surfactant. In another embodiment, the quick-breaking foaming agent does not contain a $C_1$-$C_6$ alcohol. In some embodiments, the quick-breaking foaming agent can also comprise an emollient, which can also act as a humectant. In addition, the quick-breaking foaming agent can also comprise a pH adjusting agent.

In one particular embodiment, the at least one pharmaceutically active compound is an antibiotic agent. Preferred antibiotic agents include clindamycin or a pharmaceutically acceptable salt or ester thereof. A particularly preferred antibiotic agent is clindamycin phosphate, which is inactive in vitro, but hydrolyzes in vivo to the antibacterially active clindamycin.

In another aspect, the at least one pharmaceutically active compound comprises a combination of active agents. Any combination of active agents suitable for topical administration can be used in the compositions of the present invention. Preferably, the combination of active agents comprises at least two agents selected from an antibiotic agent, an antifungal agent, a retinoid (e.g., tretinoin, tazarotene), a retinoid derivative (e.g., adapalene), salicylic acid, azelaic acid, sodium sulfacetamide, and benzoyl peroxide. Suitable antibiotic agents include, but are not limited to, clindamycin, erythromycin, tetracycline, minocycline, doxycycline, pharmaceutically acceptable salts thereof, and prodrugs thereof. More preferably, the combination of active agents comprises clindamycin phosphate and a member selected from an antifungal agent, a retinoid (e.g., tretinoin, tazarotene), a retinoid derivative (e.g., adapalene), salicylic acid, azelaic acid, sodium sulfacetamide, benzoyl peroxide, another antibiotic (e.g., erythromycin, tetracycline, minocycline, doxycycline), and mixtures thereof. In a particularly preferred embodiment, the at least one pharmaceutically active compound comprises a combination of clindamycin phosphate and tretinoin. In another particularly preferred embodiment, the at least one pharmaceutically active compound comprises a combination of clindamycin phosphate and benzoyl peroxide.

Compositions of the present invention comprising a combination of active agents preferably contain an effective amount of each agent, e.g., between about 0.01% to about 10% of an antibiotic, preferably between about 0.1% to about 5% of an antibiotic, any effective amount of salicylic acid or benzoyl peroxide, preferably between about 0.5% to about 10% w/w, and any effective amount of a retinoid or a retinoid derivative, preferably between about 0.01% to about 0.5% w/w. However, concentrations of each agent above or below the effective amount are also within the scope of the present invention.

In another embodiment, the pharmaceutically active compound is an antifungal agent. Preferred antifungal agents include ketoconazole, e.g., in the form of Nizoral®. In a further embodiment, the pharmaceutically active compound comprises a combination of an antifungal agent and an agent selected from an antibiotic agent, a retinoid (e.g., tretinoin, tazarotene), a retinoid derivative (e.g., adapalene), salicylic acid, azelaic acid, sodium sulfacetamide, benzoyl peroxide, and mixtures thereof. Suitable antibiotic agents include, but are not limited to, clindamycin, erythromycin, tetracycline, minocycline, doxycycline, pharmaceutically acceptable salts thereof, and prodrugs thereof.

In yet another aspect, the present invention provides a method for modulating the foam breaking temperature of a quick-breaking temperature sensitive foam composition. In one particular embodiment, the foam breaking temperature is modulated by, for example, changing the $C_1$-$C_6$ alcohol to water ratio in the quick-breaking temperature sensitive foam composition.

In still yet another aspect, the present invention provides a method for the percutaneous treatment of acne, using, for example, the compositions of the present invention. The acne treatment method generally involves applying a quick-breaking temperature sensitive foam composition comprising an effective amount of clindamycin or a pharmaceutically acceptable salt or a prodrug thereof to a subject in need of such treatment. In a preferred embodiment, the quick-breaking temperature sensitive foam composition further comprises a retinoid (e.g., tretinoin, tazarotene). Preferably, the retinoid is present in an amount of from about 0.01% to about 0.1% w/w. In another preferred embodiment, the quick-breaking temperature sensitive foam composition further comprises benzoyl peroxide. Preferably, the benzoyl peroxide is present in an amount of from about 0.5% to about 10% w/w.

In a further aspect, the present invention provides a method for evaluating foam characteristics, the method comprising:
  providing a visual aid comprising a depiction of various foam structures;
  dispensing a quick-breaking temperature sensitive foam composition from a pressurized container comprising a quick-breaking foaming agent and a propellant; and
  evaluating the foam structure using the visual aid.

In still yet a further embodiment, the present invention provides a use of a pharmaceutical composition in a pressurized container in the preparation of a medicament for the percutaneous treatment of acne, the composition comprising:
  up to 15% w/w of at least one pharmaceutically active compound, or its pharmaceutically acceptable salt or a prodrug thereof;
  from about 83% to about 97.9% w/w of a quick-breaking foaming agent; and
  from about 2% to about 7% w/w of an aerosol propellant selected from the group consisting of a hydrocarbon, a chlorofluorocarbon, dimethyl ether, hydrofluorocarbons and a mixture thereof,
  wherein the composition is a quick-breaking temperature sensitive foam after release from the container.

These and other objects, advantages, and embodiments will become more apparent when read with the detailed description and drawings that follow.

BRIEF DESCRIPTION OF THE DRAWINGS

FIG. 2 shows one embodiment of a visual aid that can be used in evaluating foam structures.

DETAILED DESCRIPTION OF THE INVENTION

I. Definitions

Figure 1:
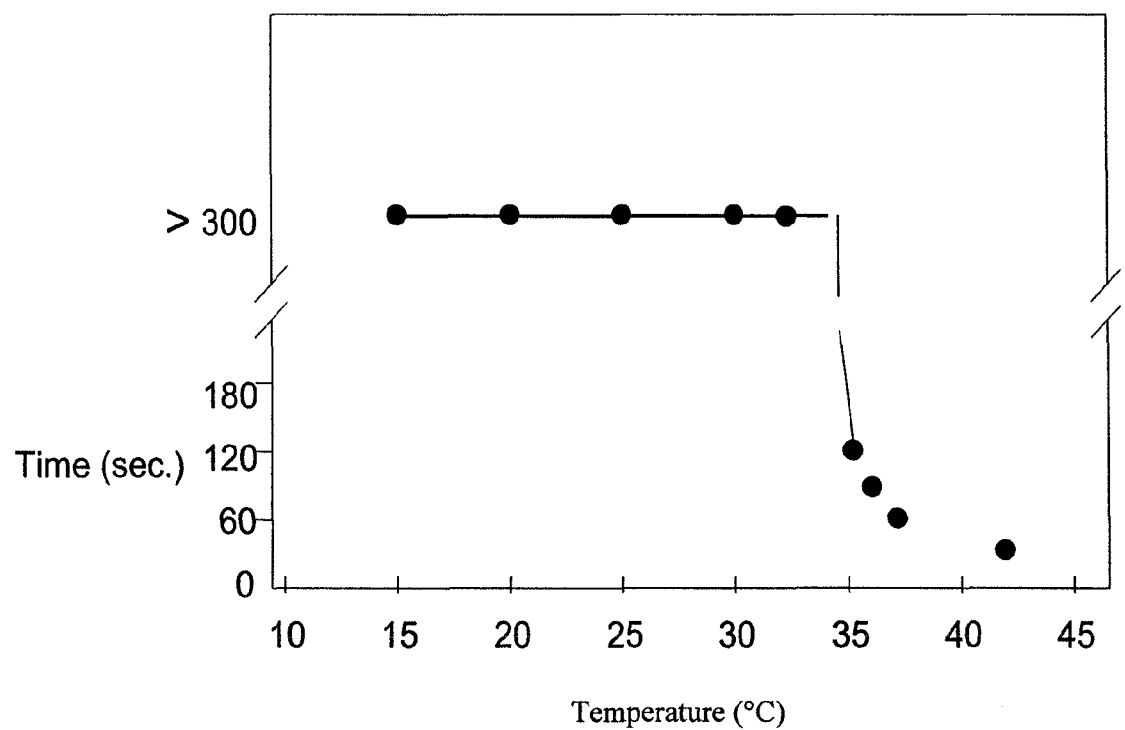
FIG. 1 is a graph showing the effect of temperature on the clindamycin phosphate foam structure, which was determined by first dispensing approximately 2 grams of foam at 20° C. The foam was then placed in a controlled environment at the indicated temperatures and the time required to melt the foam to a liquid was determined.

Unless the context requires otherwise, the terms "active agent", "active compound," "at least one pharmaceutically active compound" and "pharmaceutically active agent" are used interchangeably herein and refer to a substance having a pharmaceutical, pharmacological or therapeutic effect.

"Homogeneous" means uniform throughout, i.e., a single phase mixture.

"Pharmaceutically acceptable salt" of an active compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth metal ion, or an aluminum ion; or coordinates with an organic base such as ethanolamine, diethanolamine, triethanolamine, tromethamine, N-methylglucamine, and the like.

"Prodrug" refers to any compound which releases an active agent in vivo when such prodrug is administered to a subject. Prodrugs of an active agent are prepared by modifying one or more functional group(s) present in the active agent in such a way that the modification(s) may be cleaved in vivo to release the parent compound. Prodrugs include compounds wherein a hydroxy, amino or sulfhydryl group in the active agent is bonded to any group, e.g., protecting group, that may be cleaved in vivo to regenerate the free hydroxyl, amino or sulfhydryl group, respectively. Examples of prodrugs include, but are not limited to, active agents whose functional group(s) are protected by one or more protecting groups listed in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups which are useful in preparing prodrugs include acyl groups (e.g., formyl, acetyl and trifluoroacetyl), alkyl ethers, phosphate ethers, phosphate esters, and the like. Representative amino protecting groups that are useful in preparing prodrugs include acyl groups (e.g., formyl, acetyl, and trifluoroacetyl), benzyloxycarbonyl (CBZ), tert-butoxycarbonyl (Boc), and the like.

The terms "antibiotic" and "antibacterial" are used herein interchangeably to refer to a compound that inhibits the growth of, inhibits the virulence of, or kills bacterial cells. Antibiotics include, e.g., substances produced by various species of microorganisms (e.g., bacteria, fungi, and actinomycetes), variants thereof, and synthetic antibacterial agents. A complete list of antibiotics is too long to be included herein, and those of skill in the art are aware of the multitude of antibiotics that can be used in the present invention. See, e.g., Chambers and Sande, *Antimicrobial Agents: General Considerations in* Goodman & Gilman's The Pharmacological Basis of Therapeutics, Hardman and Limbard eds., (1996); and Kucers, et al., *The Use of Antibiotics: A Clinical Review of Antibacterial, Antifungal, and Antiviral Drugs* Oxford Univ. Press (1997). Suitable antibiotic agents include, but are not limited to, clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Preferably, the antibiotic agent is clindamycin, erythromycin, tetracycline, minocycline, doxycycline, pharmaceutically acceptable salts thereof, or prodrugs thereof. More preferably, the antibiotic agent is clindamycin, or a pharmaceutically acceptable salt or a prodrug thereof.

"Vehicle" refers to a composition which has only excipient or components required to carry an active agent, but which itself has no pharmaceutical or therapeutic effect.

The term "fatty alcohol" refers to $C_{14}$-$C_{22}$ alcohol(s).

The term "pH" is defined as the value given by a suitable, properly standardized pH meter using an appropriate electrode.

II. General

The present invention provides various pharmaceutically active topical delivery compositions. In one embodiment, a topical delivery composition in a pressurized container comprises: up to 15% w/w of at least one pharmaceutically active compound, or its pharmaceutically acceptable salt or a prodrug thereof; from about 83% to about 97.9% w/w of a quick-breaking foaming agent; and from about 2% to about 7% w/w of an aerosol propellant selected from the group consisting of a hydrocarbon, a chlorofluorocarbon, and a mixture thereof, wherein the composition is a quick-breaking temperature sensitive foam after release from the container.

In a preferred embodiment, the compositions of the present invention are present in a pressurized container comprising a homogeneous mixture of: from about 0.1% to about 10% w/w of a pharmaceutically active compound, or its pharmaceutically acceptable salt or a prodrug thereof; from about 83% to about 97.9% w/w of a quick-breaking foaming agent; and from about 2% to about 7% w/w of an aerosol propellant selected from the group consisting of a hydrocarbon, a chlorofluorocarbon, and a mixture thereof. When the above composition is released, i.e., dispensed, from a pressurized container, a quick-breaking temperature sensitive foam is formed.

The maximum amount of propellant used is often determined by its miscibility with other components in the composition to form a mixture, such as a homogeneous mixture. The minimal level of propellant used in the composition is often determined by the desired foam characteristics, and its ability to substantially or completely evacuate the container.

The quick-breaking foaming agent comprises water and a surfactant, or a combination of surfactants, and an optional component(s), such as a $C_1$-$C_6$ alcohol, a $C_{14}$-$C_{22}$ alcohol, and combinations thereof. In some embodiments, the quick-breaking foaming agent can also comprise an emollient, which can also act as a humectant.

Suitable emollients include, but are not limited to, polyols. Preferred polyols include propylene glycol and glycerol. The amount of emollient used in the quick-breaking foaming agent varies from about 0% to about 20% w/w, preferably from about 0% to about 10% w/w, and more preferably from about 2% to about 7.5% w/w.

In one embodiment, the quick-breaking foaming agent comprises a $C_1$-$C_6$ alcohol and water. In a preferred embodiment, the quick-breaking foaming agent comprises a $C_1$-$C_6$ alcohol, a $C_{14}$-$C_{22}$ alcohol, water, and a surfactant. In an alternative embodiment, the quick-breaking foaming agent does not contain a $C_1$-$C_6$ alcohol.

In addition, the quick-breaking foaming agent can also comprise a pH adjusting agent. In one particular embodiment, the pH adjusting agent is a base. Suitable pH adjusting bases include bicarbonates, carbonates, and hydroxides such as alkali or alkaline earth metal hydroxide as well as transition metal hydroxides. Preferably, the pH adjusting agent is potassium hydroxide. Alternatively, the pH adjusting agent can also be an acid, an acid salt, or mixtures thereof. Further, the pH adjusting agent can also be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. The pH adjusting agent is present in an amount sufficient to adjust the pH of the composition to between about pH 4.0 to about 9.0, preferably about pH 4.0 to about 6.5.

Preferably, the quick-breaking foaming agent composition comprises a $C_1$-$C_6$ alcohol, more preferably a $C_1$-$C_4$ alcohol, such as methanol, ethanol, propanol e.g., isopropanol, butanol, and a mixture of two or more thereof. A particularly preferred $C_1$-$C_6$ alcohol is ethanol or a mixture of ethanol with and at least one other alcohol. The amount of $C_1$-$C_6$ alcohol used in the quick-breaking foaming agent varies from about 0% to about 95% w/w, preferably from about 55% to about 65% w/w, and more preferably from about 58% to about 60% w/w.

The amount of $C_{14}$-$C_{22}$ alcohol in the quick-breaking foaming agent varies from about 0% to about 10% w/w, preferably from about 1% to about 5.0% w/w. In certain aspects, the quick-breaking foaming agent preferably comprises from about 1% to about 2.5% w/w of the $C_{14}$-$C_{22}$ alcohol. An especially preferred amount of $C_{14}$-$C_{22}$ alcohol in the quick-breaking foaming agent is from about 1.5% to about 2% w/w.

A preferred $C_{14}$-$C_{22}$ alcohol in the quick-breaking foaming agent is a $C_{16}$-$C_{20}$ alcohol. In particular, cetyl alcohol, stearyl alcohol, or a mixture thereof is particularly preferred. Especially preferred is a mixture of cetyl alcohol and stearyl alcohol. The ratio of cetyl alcohol to stearyl alcohol can range from about 60:40 to about 80:20, with the ratio of about 70:30 being a preferred mixture ratio.

A wide variety of surfactants are useful in compositions of the present invention including, for example, ethoxylated non-ionic and ethoxylated ionic surfactants. Suitable surfactants for use in compositions of the present invention include, but are not limited to, fatty acid ethoxylates, fatty alcohol ethoxylates, polysorbates, glycerol ester ethoxylates, and block copolymers such as poloxamers. Examples of these include Polysorbate 20, Polysorbate 60, Polysorbate 80, Laureth-4, Laureth-23, POE(15) glycerol monolaurate, and the like. In a particularly preferred embodiment, the surfactant is Polysorbate 60, Laureth-4, POE(15) glycerol monolaurate, or mixtures thereof. The amount of surfactant present in the quick-breaking foaming agent generally ranges from about 0% to about 10% w/w, preferably from about 0.1% to about 10% w/w, more preferably from about 0.1% to about 6% w/w, with from about 0.5% to about 5% w/w and from about 0.3% to about 0.5% w/w being especially preferred amounts.

Water, and optionally, a pH adjusting agent, generally comprises the remaining portion of the quick-breaking foaming agent. The amount of water present in the quick-breaking foaming agent ranges from about 10% to about 95% w/w, preferably from about 10% to about 90% w/w, more preferably from about 20% to about 90% w/w, with from about 30% to about 40% w/w, or alternatively from about 80% to about 95% w/w, being especially preferred.

While a typical amount of each component of the quick-breaking foaming agent is provided above, it should be appreciated that a particular amount of each component of the quick-breaking foaming agent depends on the foam characteristics desired. Therefore, the scope of the present invention is not limited to those values provided herein.

In certain aspects, the quick-breaking temperature sensitive foam is formulated such that the foam breaking temperature is at or near skin temperature. The foam breaking temperature can be modulated by changing the ratio of various components of the quick-breaking foaming agent, e.g., the $C_1$-$C_6$ alcohol to water ratio. In one particular embodiment, the foam breaking temperature can be adjusted to be from about 30° C. to about 36° C., such as 30° C., 31° C., 32° C., 33° C., 34° C., 35° C., and 36° C. For example, a particularly preferred foam breaking temperature for clindamycin foam is 35° C.

Preferably, the pressurized container is a one-piece aluminum container in which the inner surface is lined with a chemically inert lining. A preferred inner surface lining is polyamide-imide (PAM) lacquer, supplied by HOBA Lacke and Farben GmbH. Typically, the container is fitted with an upright or inverted valve and a conventional foam spout actuator.

In addition, the present invention provides various aspects related to such compositions, including: methods for modulating a foam characteristic; methods for improving the shelf-life of a pharmaceutically active compound or its pharmaceutically acceptable salt or a prodrug thereof; methods for percutaneous treatment of various diseases, infections, and illnesses; and methods for evaluating foam characteristics.

III. Antibiotic Formulation

In one embodiment, the at least one pharmaceutically active compound is an antibacterial agent. Suitable antibacterial agents include, but are not limited to, clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Preferably, the antibacterial agent is clindamycin, or a pharmaceutically acceptable salt or a prodrug thereof.

Clindamycin is an antibiotic also known as methyl 7-chloro-6,7,8-trideoxy-6-(1-methyl-trans-4-propyl-L-2-pynolidinecarboxamido)-1-thio-L-threo-α-D-galacto-octo-pyranoside or methyl 7-chloro-6,7,8-trideoxy-6-[[(1-methyl-4-propyl-2-pyrrolidinyl)carbonyl]amino]-1-thio-L-threo-α-D-galacto-octo-pyranoside. As used herein, the term "clindamycin" alone includes free-base clindamycin as well as the pharmaceutically acceptable salts and esters thereof. Examples of pharmaceutically acceptable salts and esters of clindamycin include, but are not limited to, clindamycin hydrochloride, clindamycin phosphate, clindamycin palmitate, and clindamycin palmitate hydrochloride. It is preferred to use a clindamycin salt or ester in the compositions of the present invention, with clindamycin phosphate being especially preferred.

Suitable concentration ranges of the at least one pharmaceutically active compound include, for example, from about 0.001% to about 50% w/w, preferably from about 0.01% to about 20% w/w, such as up to 15% w/w, and more preferably from about 0.1% to about 2% w/w. About 1% w/w is especially preferred.

The uses, properties, and methods of synthesis of clindamycin are set forth in U.S. Pat. No. 3,969,516, Stoughton, issued Jul. 13, 1976; U.S. Pat. No. 3,475,407, Bierkenmeyer, issued in 1969; U.S. Pat. No. 3,487,068, issued in 1969; U.S. Pat. Nos. 3,509,127 and 3,544,551, Kagan and Magerlein, issued in 1970; U.S. Pat. No. 3,513,155, Bierkemeyer and Kagan, issued in 1970; Morozowich and Sinkula, U.S. Pat. No. 3,580,904, issued in 1971 and U.S. Pat. No. 3,655,885, issued in 1972; U.S. Pat. No. 3,714,141, issued in 1973; U.S. Pat. No. 4,568,741, issued in 1986; and U.S. Pat. No. 4,710,565, issued in 1984. All of the foregoing patents are incorporated herein by reference.

Additional knowledge in the art concerning clindamycin is found in, for example, Magerlein, et al., *Antimicro. Ag. Chemother.* 727 (1966); Birkenmeyer and Kagan, *J. Med. Chem.*, 13, 616 (1970); Oesterling, *J. Pharm Sci.* 59, 63 (1970); McGehee, et al., *Am. J. Med. Sci.* 256, 279 (1968); D. A. Leigh, *J. Antimicrob. Chemother.* 7 (Supplement A), 3 (1981); J E Gray et al., *Toxicol. Appl. Pharmacol.* 21, 516 (1972), and L W Brown and W F Beyer in *Analytical Profiles of Drug Substances*, Vol. 10, K. Florey, editor (Academic Press, New York, 1981), pages 75-91.

It will be particularly apparent to those of skill in the art that the development of a clindamycin foam composition is especially surprising. First of all, clindamycin, such as clindamycin phosphate, is a water soluble pharmaceutical agent. In order to make the foam composition a quick-breaking foam composition, the melting point of the composition needed to be within the temperature ranges already set forth (e.g., at or near skin temperature). In certain instances, the melting point needed to be adjusted and raised, which was difficult due to the water solubility of clindamycin and the high concentrations of clindamycin used. These difficulties were overcome in part by adjusting the $C_1$-$C_6$ alcohol to water ratios, such as the ethanol to water ratio.

Moreover, high concentrations of active compounds can also impact foam structure and foam quality, as well as cause unwanted crystallization. Water-soluble active compounds can, in effect, remove water from the system, virtually changing the ratio of water to $C_1$-$C_6$ alcohol, and therefore the foam characteristics, including the melting point. This may require intervention to achieve an acceptable foam quality. The $C_1$-$C_6$ alcohol may not be a good solvent for water-soluble active compounds, allowing crystallization at lower temperatures. Simply increasing the water content to prevent crystallization will alter the foam characteristics and will change the solubility of the fatty alcohols, possibly causing them to precipitate. Crystallization can lead to loss of pharmaceutically active compounds and/or blockage of the aerosol valve.

Figure 3:
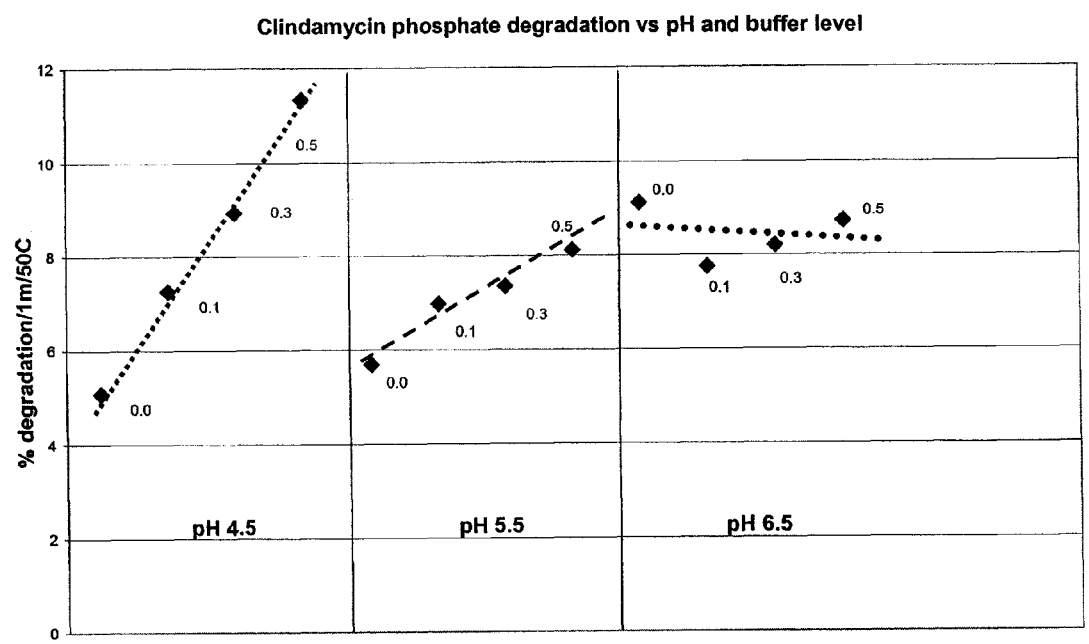
FIG. 3 is a graph showing the amount of clindamycin phosphate degradation at various pH and citrate buffer levels as described in Example 1.

Addition of a buffer is often used to improve the stability of an active compound, and, in the case of aerosol containers, to reduce corrosion of the metal. In certain instances, the buffer can make the formulation less stable rather than more stable. In these cases, e.g., for clindamycin phosphate compositions, a pH adjustment rather than full buffering may be more effective. This is shown in FIG. 3, where higher levels of buffer cause more degradation rather than less degradation.

In certain preferred embodiments, clindamycin phosphate is the active agent and the quick-breaking foaming agent comprises a mixture of cetyl alcohol and stearyl alcohol, which are dissolved in a water/ethanol solution. Preferably, this composition is packaged in a polyamide-imide-lined aluminum can and pressurized with a propane/butane mixture as the propellant. Under the packaged pressure, the hydrocarbon propellant liquefies and becomes miscible with the water/ethanol solution. This liquefied hydrocarbon/water/ethanol solution allows increased solubility of the cetyl and stearyl alcohols compared to water/ethanol solutions alone. At temperatures above 11° C., the contents of the can under pressure remain as a clear homogeneous solution. Without being bound by any particular theory, it is believed that the foam structure, i.e., characteristic, which is formed when the composition is released from the can is controlled by the solubility of the fatty alcohols (e.g., a mixture of cetyl alcohol and stearyl alcohol) in the aqueous/ethanolic solution. Upon dispensing, the propellant expands and vaporizes, allowing the fatty alcohols (e.g., a mixture of cetyl alcohol and stearyl alcohol) to form a stable foam structure. Thus, the ratios and choice of these components (e.g., water:ethanol:cetyl alcohol:stearyl alcohol) affect the physical characteristics of the foam.

Preferably, the water, ethanol, and propellant levels are selected to provide the minimum solubility of the fatty alcohols in the can. In certain aspects, the present inventors have discovered that a change in the water:ethanol ratio alters foam characteristics. For example, an increase in the water:ethanol ratio leads to a decrease in solubility of the fatty alcohols and an ensuing solidification of the foam structure. Conversely, a decrease in the water:ethanol ratio leads to an increase in solubility of the fatty alcohols and results in the formation of a more fluid foam.

Polysorbate is used as the preferred surfactant, with Polysorbate 60 being an especially preferred surfactant. Without being bound by any theory, in addition to its role in foam formation, it is believed that Polysorbate 60 enhances cetyl alcohol and/or stearyl alcohol solubility.

The topical delivery composition of clindamycin phosphate is typically accomplished by first dissolving the components into either water or ethanol. Due to their limited solubility in water, cetyl alcohol and stearyl alcohol are dissolved in the ethanolic phase. Polysorbate 60 and propylene glycol (i.e., an emollient which also can act as a humectant) are soluble in both ethanol and water, but for convenience are dissolved in the ethanolic phase. Clindamycin phosphate and potassium hydroxide (i.e., a pH adjusting agent) are dissolved in water. The aqueous and ethanolic phases are then added at the appropriate ratio into the individual cans during the filling operation. The valves are fitted to the cans and crimped into place. A metered amount of propellant is then injected through the valve to complete the formulation. Another means of filling the cans involves a single-liquid-phase fill, in which the composition is kept warm to ensure homogeneity, followed by crimping and propellant injection. Yet another means involves formulating the entire composition, including the propellant, in bulk, under pressure, and then injecting the formulation into the crimped aerosol can.

A typical topical delivery clindamycin phosphate composition of the present invention, excluding the amount of propellant, is shown in Table 1 below.

TABLE 1

A representative topical delivery clindamycin phosphate composition of the present invention.

| Component | Amount (% w/w) |
|---|---|
| Clindamycin phosphate, USP (calculated as clindamycin) | 1.25 |

TABLE 1-continued

A representative topical delivery clindamycin phosphate composition of the present invention.

| Component | Amount (% w/w) |
|---|---|
| Dehydrated Alcohol (Ethanol), USP | 58.21 |
| Cetyl Alcohol, NF | 1.16 |
| Stearyl Alcohol, NF | 0.53 |
| Polysorbate 60, NF | 0.42 |
| Propylene Glycol, USP | 2.11 |
| Purified Water, USP | 36.21 |
| Potassium Hydroxide, USP, 10% w/w soln. | 0.11 |

The amount of clindamycin phosphate is based on its purity (typically 800 mg/g calculated as clindamycin), and is adjusted to provide 1.00% calculated as clindamycin in the final composition, as shown in Table 1. Thus, the exact amount of clindamycin phosphate can vary depending on its purity.

In a preferred aspect, the amount of propellant added to the topical delivery clindamycin phosphate composition is about 2.8 g of propane/butane propellant for each about 50 g of the above mixture. In addition to its function as a propellant and for creating the microstructure of the foam upon dispensing, the hydrocarbon or mixtures thereof helps to dissolve the cetyl alcohol and stearyl alcohol in the aqueous/ethanolic system to produce a clear, one-phase (i.e., homogeneous) system in the container. Typically, the range of propellant concentration is from about 2% to about 7% w/w relative to the total amount of composition, preferably from about 3% to about 6% w/w, and more preferably in the range of from about 4.6% to about 5.4% w/w.

While chlorofluorocarbons (CFCs) can also be used as propellants, due to environmental concerns the preferred propellants are hydrocarbons, in particular, propane, butane, or a mixture thereof. Other suitable propellants include dimethyl ether and hydrofluorocarbons such as 134a and 227. An especially preferred propellant is a mixture of propane and butane.

Table 2 below summarizes some of the functions of each component in the clindamycin phosphate compositions of the present invention.

TABLE 2

Some of the functions of ingredients in clindamycin phosphate compositions of the present invention.

| Component | Purpose |
|---|---|
| Clindamycin phosphate | Active ingredient; topical anti-microbial |
| Cetyl Alcohol, NF | Maintains foam characteristics |
| Stearyl Alcohol, NF | Maintains foam characteristics |
| Polysorbate 60, NF | Enhances solubility of cetyl alcohol and stearyl alcohol and enhances foam formation. |
| Dehydrated Alcohol (Ethanol), USP | Solvent for the active ingredient, and for cetyl alcohol and stearyl alcohol |
| Purified Water, USP | Solvent, Moisturizer |
| Propylene Glycol, USP | Humectant |
| Potassium Hydroxide, USP | pH control |
| Propane/Butane Propellant (70 psig) | Dissolves cetyl alcohol and stearyl alcohol in the aqueous/ethanolic system to produce a clear, one-phase system, propels the product from the can, and creates the microstructure of the foam upon dispensing |

Typically, the pressurized container is fitted with a dip tube; hence, the composition is dispensed by holding the can upright and depressing the actuator button. The dispensed foam is thermolabile, i.e., a quick-breaking temperature sensitive foam. Preferably, the foam structure collapses at, i.e., the foam breaking temperature is, approximately skin temperature, preferably between about 30° C. to about 36° C., with the foam breaking temperature of about 35° C. being especially preferred. This allows the dispensing of a relatively stiff foam at ambient temperature and the subsequent breakdown of the foam structure upon contact with the skin. Thus, the clindamycin phosphate quick-breaking temperature sensitive foam (i.e., clindamycin phosphate foam) of the present invention can be directly applied to easily targeted areas.

For less accessible areas, the clindamycin phosphate foam is generally dispensed onto a convenient surface prior to topical application. The thermolabile nature of the clindamycin phosphate foam requires the dispensing of the composition onto a saucer, the cap of the can, or other cool surface so as to maintain the integrity of the foam structure. The clindamycin phosphate foam can then be applied with a hand or an applicator.

The thermolabile qualities of the dispensed foam vehicle as a function of temperature are shown in FIG. 1, which shows a critical temperature, i.e., foam breaking temperature, of about 35° C. Below this temperature, the foam remains quite stable and retains structural integrity for over 5 minutes. Above 35° C., the cetyl and stearyl alcohol redissolve and the foam breaks down.

The quality of the clindamycin phosphate foam is also affected by the ambient temperature. For example, containers stored at higher temperatures (i.e., between 28° C. and 34° C.) dispense a softer clindamycin phosphate foam than those dispensed at lower temperatures (i.e., below 25° C.). A general description of clindamycin phosphate foam quality as a function of container temperature is shown in Table 3 below.

TABLE 3

Container Temperature and its Effect on Clindamycin Phosphate Foam Quality.

| Temperature | Foam Quality Description |
|---|---|
| Ambient temperatures below 25° C. | Crisp, dry, well maintained shape. Foam has very fine bubbles. A small scoop taken from the foam creates a hole with well defined edges. Foam does not slide when surface is tilted. |

TABLE 3-continued

Container Temperature and its Effect on Clindamycin Phosphate Foam Quality.

| Temperature | Foam Quality Description |
| --- | --- |
| 31° C. | Soft, slightly flowing. Foam has fine bubbles. A small scoop taken from the foam creates a hole with softer, rounded edges. Foam does not slide when surface is tilted. |
| 34° C. | Very soft, moderately flowing. Foam has visibly larger bubbles. A small scoop taken from foam creates a hole that slowly flows together. Foam slowly slides when surface is tilted. |
| 37° C. | Runny, weak, flowing. Foam composed of relatively large bubbles. Scooping tends to disrupt the bubbles breaking the foam structure. Foam readily slides when surface is tilted. |

As shown in Table 3, a preferred clindamycin phosphate foam dispensing temperature is between about 23° C. to about 27° C., such as 25° C. or below. However, the temperature effects on foam formation are reversible. Thus, cooling a warmed container that dispenses a soft clindamycin phosphate foam to below 25° C. will dispense an acceptable crisp, dry foam.

The preferred propellant for use in the clindamycin phosphate foam compositions of the present invention comprises a propane and butane mixture. A particularly preferred propellant comprises a mixture of propane, n-butane, and isobutane. A propellant composition comprising about 55% propane, about 30% n-butane, and about 15% isobutane is especially preferred.

Without being bound to any particular theory, it is believed that upon dispensing the composition from the container, the propellant in the solution evaporates or vaporizes and creates the bubbles of the foam structure. Some of this vaporized propellant is quickly released and dispersed to the atmosphere while the remainder is trapped within the foam structure.

IV. Foam Characteristics Modification

Another aspect of the present invention provides a method for modulating a foam characteristic of a quick-breaking temperature sensitive foam composition by changing the $C_1$-$C_6$ alcohol to water ratio in the quick-breaking foaming agent. In this manner, a variety of foam characteristics can be modified, including, but not limited to, clarity, density, viscosity, foam bubble size, foam expansion rate, foam flow rate, and/or foam breaking temperature.

In one embodiment, the $C_1$-$C_6$ alcohol to water ratio ranges from about 1.5:1 to about 1.8:1, preferably from about 1.55:1 to about 1.75:1, and more preferably from about 1.6:1 to about 1.7:1. In another embodiment, the $C_1$-$C_6$ alcohol to water ratio is less than about 1:7. In yet another embodiment, the $C_1$-$C_6$ alcohol to water ratio ranges from about 1:7 to about 1:16, and is preferably about 1:7 or about 1:16.

In a further embodiment, the $C_1$-$C_6$ alcohol to water ratio in the quick-breaking foaming agent is modified to achieve a desired foam breaking temperature. Table 4 below shows the effect of the ethanol to water ratio on the melting point (i.e., foam breaking temperature) of clindamycin phosphate foam. As shown in Table 4, a foam breaking temperature of 35° C. is achieved by adjusting the ratio of ethanol to water to 1.60:1. This formulation was used in determining the thermolabile quality as shown in FIG. 1.

TABLE 4

Foam Breaking Temperature vs. Ethanol to Water Ratio.

| | Ethanol:Water ratio | | | | |
| --- | --- | --- | --- | --- | --- |
| | 1.66:1 | 1.64:1 | 1.62:1 | 1.60:1 | 1.58:1 |
| Melting Point (° C.) | 32 | 33 | 34 | 35 | 36 |

V. Utility

Clindamycin phosphate foam compositions of the present invention are useful in treating various bacteria-mediated diseases or illnesses via topical application, e.g., in treating acne vulgaris and bacterial vaginosis. Analogously, other antibacterial agents or their corresponding prodrugs can be used instead of clindamycin to treat other bacteria-mediated diseases or illnesses. Suitable additional antibacterial agents include, but are not limited to, erythromycin, tetracycline, minocycline, doxycycline, pharmaceutically acceptable salts thereof, and prodrugs thereof. Furthermore, antifungal agents such as ketoconazole can be used to treat fungal infections such as athlete's foot and the like.

It should be appreciated that when another pharmaceutical compound is used instead of clindamycin phosphate, one or more components of the composition (e.g., the quick-breaking foaming agent and/or the propellant) can be modified or its amount adjusted to achieve a desired foam characteristic (e.g., smoothness of the foam, the foam breaking temperature, stability of the active compound, and the like).

VI. Foam Evaluation

In another aspect, the present invention provides a method for evaluating foam characteristics. Such a method generally involves providing a visual aid that depicts various foam structures or characteristics, dispensing the foam, and evaluating the foam structure using the visual aid (e.g., look-up table). Exemplary characteristics that can be depicted in the visual aid include shape, structure, clarity, density, viscosity, foam bubble size, foam expansion rate, foam flow rate, and foam breaking temperature. One or more of these characteristics can be depicted in a visual aid such as a look-up table.

The visual aid (e.g., look-up table) can comprise one or more methods that describe the foam structure or characteristics, such as a visual depiction (e.g., pictures either in a hard copy form or a digital, i.e., electronic form) of various foam structures, numeric and/or alphanumeric values for each foam structure (e.g., look-up values) and/or a literal description of each foam structure. The visual aid is typically prepared by generating different foam structures at various amounts of one or more components of the quick-breaking temperature sensitive foam composition. An exemplary visual aid is shown in FIG. 2, which provides various formats, i.e., visual, numeric, and literal, for evaluating the foam characteristics. These look-up tables and visual aids are especially useful for research and development, good manufacturing practice (GMP) and quality control (QC) methods.

In one embodiment, the foam to be evaluated is a quick-breaking temperature sensitive foam composition, which is dispensed from a pressurized container comprising a quick-breaking foaming agent and a propellant. The foam composition can also comprise a pharmaceutically active compound or its pharmaceutically acceptable salt or a prodrug thereof.

Additional objects, advantages, and novel features of this invention will become apparent to those skilled in the art upon examination of the following examples thereof, which are not intended to be limiting.

EXAMPLES

The following examples are offered to illustrate, but not to limit, the claimed invention.

Example 1

This example illustrates the effect of pH on the stability of clindamycin phosphate using a citrate buffer solution and an epoxy-phenolic lined container.

Clindamycin phosphate foam composition samples similar to Table 1 were prepared in aluminum aerosol cans with a standard epoxy-phenolic (epon) lining and fitted with a valve from the Precision Valve Company. In this study, a citrate buffer solution was used to adjust the pH of the mixture to pH 4.5, pH 5.5, and pH 6.5 using four different buffer concentrations (i.e., 0, 0.1, 0.3, 0.5%) and two alternative emollients or humectants, i.e., propylene glycol and glycerin. The containers were stored at 50° C. for 1 month and then examined. The results are shown in FIG. 3.

As shown in FIG. 3, higher buffer levels (e.g., 0.5%, 0.3%) result in a higher amount of clindamycin phosphate degradation than lower buffer levels (e.g., 0.1%, 0.0%). Moreover, clindamycin phosphate is more stable at a lower pH level.

Example 2

This example illustrates the effect of pH on the stability of clindamycin phosphate using different inner-lining materials in the container. Generally, the procedure of Example 1 was followed except as indicated below.

Low buffer levels at a pH of 4.5 or 6.5, including unbuffered pH 4.5, were tested in cans with either epoxy-phenolic, polyamide-imide (PAM), or Micoflex linings. Some of the PAM-lined cans were scratched internally to check for corrosion on bare aluminum. Cans were stored at 4° C., 40° C., and 50° C. for 4 weeks and then examined. The results are shown in FIG. 4.

Figure 4:
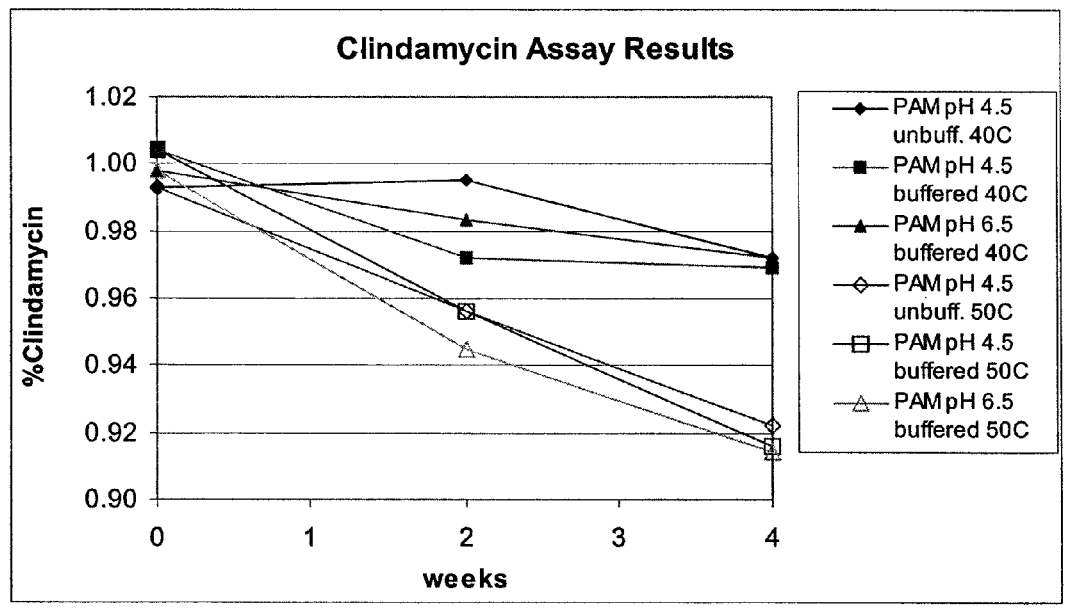
FIG. 4 is a graph showing the amount of clindamycin phosphate remaining at various times under various pH levels in cans at various temperatures.

As shown in FIG. 4, the presence of a buffer solution is not necessary to the stability of clindamycin phosphate. In addition, the PAM-lined container afforded unexpectedly high clindamycin phosphate stability. Moreover, intentionally internally scratched containers resulted in eventual leakage of can contents. Thus, the integrity of the container lining is important in maintaining the stability of clindamycin phosphate.

In general, a relatively severe degradation of clindamycin phosphate was observed at 50° C., and a moderate degradation of clindamycin phosphate was observed at 40° C. However, since clindamycin phosphate is unstable at 50° C. (data not shown), tests at this temperature cannot be used to predict its stability at ambient temperature. As expected, in general, degradation of clindamycin phosphate is more rapid at higher temperatures.

Example 3

This example illustrates the effect of pH on the stability of clindamycin phosphate using potassium hydroxide as a pH adjusting agent. Generally, the procedure of Example 1 was followed except as indicated below.

Two pH levels of the clindamycin phosphate foam composition were tested: an unadjusted "natural" pH of 4.5; and an adjusted pH of 5.5 using potassium hydroxide. Cans tested were lined with PAM or Micoflex linings. PAM-lined cans that were scratched internally were also tested. Samples were stored at 4° C., 25° C., 40° C., and 50° C. for up to 12 months.

This testing led to the selection of the formulation shown in Table 1 above, with a target pH of 5.0 (pH of formulated base at 40° C.). This pH is adjusted with potassium hydroxide. PAM was confirmed as a preferred container lining for clindamycin phosphate foam compositions.

Further testing revealed that about 0.11% of a 10% potassium hydroxide solution, as shown in Table 1, was needed to achieve a pH of about 5.

Example 4

This example shows the stability of clindamycin phosphate under various conditions.

At each time/temperature point for the above stability experiments (i.e., Examples 1, 2, and 3), the following parameters were also measured: weight loss, spray rate, pressure, pH (pH of degassed base at 40° C.), potency (clindamycin phosphate concentration by HPLC), appearance upon dispensing and melting, and can lining and valve interactions.

Negligible changes in spray rate, pressure, or appearance upon dispensing and melting were observed over the course of the study either between temperatures or over time. Can lining interactions were observed in the early studies on epoxy-phenolic linings only; no valve interactions were observed.

Figure 5:
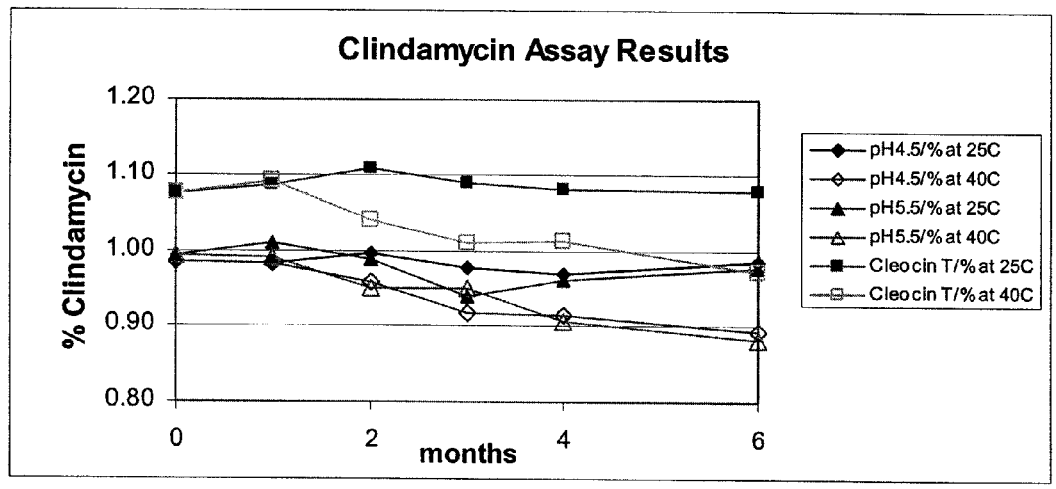
FIG. 5 shows stability data of clindamycin phosphate as determined in Example 4.

The results of the weight loss, pH, and potency tests for this stability trial are shown in FIG. 5. As shown in FIG. 5, there is a minimal change in the concentration of clindamycin phosphate for pH 4.5 and pH 5.5 at 25° C. over 6 months, whereas at 40° C. a decrease of almost 10% was observed. The degradation of clindamycin phosphate in Cleocin T showed a similar pattern. Overall, this data indicated good stability of the clindamycin phosphate at normal storage temperatures. The major degradant was clindamycin base.

Both formulations, pH 4.5 (natural pH) and pH 5.5 (adjusted pH), showed a slight weight loss at 4° C. and 25° C., but increased rates of weight loss as the temperature was increased. After three months of storage, losses of approximately 0.10 g, 0.25 g, and 0.45 g were recorded at 25° C., 40° C., and 50° C., respectively.

Example 5

This example illustrates the stability of clindamycin phosphate in the clindamycin phosphate foam compositions of the present invention.

Clindamycin phosphate foam compositions similar to that shown in Table 1 above were stored at 25° C. and 40° C. Each foam composition was analyzed each month for appearance (e.g., foam characteristics such as color), pH, and the relative amount of clindamycin phosphate, which was analyzed using HPLC. The stability test results at various time intervals, i.e., at 0-9 months, are shown in Table 5.

TABLE 5

Stability Test Results of 1% Clindamycin Phosphate Foam.
Container: 35 × 125 mm aluminum can
Closure: 1" Aluminum cup dip tube

| Methods | | Appearance | Apparent pH | Prod. & Pack. Inter. | Total Clindamycin (% w/w) | Clindamycin (% w/w) | Related Substances (% peak area) |
|---|---|---|---|---|---|---|---|
| Storage | Month | See A | Report | See B | 0.90-1.10 | ≤0.10 | Report |
| 25° C./ | 0 | Pass | 5.0 | Pass | 0.97 | 0.004 | 1.23 |
| 50% RH | 1 | Pass | 5.0 | Pass | 1.03 | 0.004 | 0.89 |
| | 2 | Pass | 5.3 | Pass | 1.02 | 0.006 | 1.26 |
| | 3 | Pass | 5.0 | Pass | 1.01 | 0.008 | 0.45 |
| | 6 | Pass | 4.9 | Pass | 1.00 | 0.009 | 1.37 |
| | 9 | Pass | 5.4 | Pass | 1.01 | 0.013 | 0.54 |
| 40° C./ | 0 | Pass | 5.0 | Pass | 0.97 | 0.004 | 1.23 |
| 75% RH | 1 | Pass | 5.0 | Pass | 1.02 | 0.013 | 1.06 |
| | 2 | Pass | 5.3 | Pass | 1.04 | 0.025 | 0.79 |
| | 3 | Pass | 4.9 | Pass | 1.01 | 0.032 | 0.37 |
| | 6 | Pass | 4.8 | Pass | 0.99 | 0.062 | 1.92 |
| | 9 | Pass | 5.2 | Pass | 0.99 | 0.097 | 0.76 |

A = Upon actuation, a white foam is produced. At 40° C., the product is a clear, colorless to pale yellow solution with no visible foreign matter.
B = No visible evidence of product interaction with can, lining, or valve.

Example 6

This example illustrates a clinical trial for evaluating the effectiveness of the clindamycin phosphate foam of the present invention.

The clinical trial was conducted at multiple centers. A total of 125 male and female subjects, 12 years of age or older, with mild to moderate acne vulgaris were selected for a randomized, double-blinded test. Each subject received one of the three treatments: 1% clindamycin phosphate foam, vehicle foam (i.e., placebo), or 1% clindamycin phosphate topical gel. Subjects were randomized in a 2:1:2 ratio (clindamycin phosphate foam:placebo:clindamycin phosphate gel).

Subjects were assigned to a treatment group upon randomization. Subjects and nurses/coordinators were un-blinded to the form of study medication assigned (foam or gel). Assignment to the foam treatment group (active or placebo) was blinded for subjects, nurses/coordinators, and investigators. The investigators/designee (i.e., person who has been trained and assigned to perform efficacy evaluations) were blinded to the form of study medication assigned (foam or gel) and subjects were instructed to not to discuss this information with the investigator/designee.

The study duration was 12 weeks with visits at baseline (week 0, day 1), week 3, week 6, week 9, and week 12. All treatments were administered once daily (morning or evening) for 12 weeks. Approximately fifty subjects were randomly assigned to treatment with clindamycin phosphate foam, approximately twenty five subjects were randomly assigned to placebo, and approximately fifty subjects were randomly assigned to clindamycin phosphate gel. Subjects applied a sufficient amount of study medication to cover the entire face. If the subject had neck, upper chest, and/or upper back acne, he or she was allowed to apply the study medication to those areas as well. However, the neck, upper chest, and upper back areas were not included in the efficacy evaluation.

Efficacy of the study medication was evaluated based on lesion counts (total, inflammatory, and non-inflammatory) and an investigator's static global assessment (5-point scale) at baseline and at weeks 3, 6, 9, and 12. At week 12, an additional investigator's static global assessment utilizing a 6-point scale was performed. In addition, a subject's global assessment was made at baseline and at weeks 3, 6, 9, and 12. The efficacy results are shown in Table 6 below and illustrate that the inventive foam has superior efficacy.

TABLE 6

Efficacy Study Results.

| | Inventive Foam | Comparative Gel | Placebo |
|---|---|---|---|
| Number of Subjects | 49 | 46 | 24 |
| Total Lesions (median) | −46.2 | −41.1 | −32.8 |
| Inflammatory Lesions (median) | −60.0 | −54.4 | −38.5 |
| Non-inflammatory Lesions (median) | −38.5 | −25.0 | −28.5 |

As the efficacy study results show, the clindamycin phosphate foam composition of the present invention is significantly more effective than the clindamycin gel composition that is currently available.

Example 7

This example illustrates a second clinical trial with more subjects for evaluating the effectiveness of the clindamycin phosphate foam of the present invention.

A 12-week, multi-center (18 sites), randomized, double-blind, double-dummy, vehicle-controlled study of 1026 male and female subjects, 12 years of age or older, with mild to moderate acne vulgaris was conducted. Subjects had an Investigator's Static Global Assessment (ISGA) of 2 or greater (see, Table 7), 17-40 facial inflammatory lesions (papules plus pustules) including nasal lesions, and 20-150 facial non-inflammatory lesions (open and closed comedones) excluding nasal lesions.

Subjects were in good general health. Excluded from participation were those who had any active nodulo-cystic lesions or a history of regional enteritis or inflammatory bowel disease. Subjects were also excluded from participation if they had used the following to treat their acne: systemic antibiotic or steroid therapy within the prior 4 weeks; systemic retinoids within the prior 3 months; or topical anti-acne medications or topical antibiotics in the prior 4 weeks. Subjects were also excluded if their estrogen or androgen use had changed within 12 weeks or less, or if they intended to use any of the following types of products or procedures concomitantly: benzoyl peroxide, salicylic acid, retinol, α- or β-hydroxy acids, neuromuscular blocking agents, tanning booths, sunbathing, facial procedures (e.g., chemical or laser peels), or medications known to exacerbate acne.

Subjects were enrolled and randomized to receive one of four treatments in a 3:3:1:1 ratio: (1) 1% clindamycin phosphate foam; (2) 1% clindamycin phosphate gel; (3) vehicle foam; or (4) vehicle gel. The study duration was 12 weeks with visits at Baseline and Weeks 3, 6, 9, and 12. All treatments were administered once daily (i.e., morning or evening) for 12 weeks.

Efficacy of each treatment was evaluated by performing acne lesion counts (total, inflammatory, and non-inflammatory), an Investigator's Static Global Assessment of facial acne vulgaris, and a Subject's Global Assessment at each visit. Safety was assessed from vital signs, clinical laboratory assessments, and reported adverse events. Additionally, evaluations of the severity of the signs (e.g., scaling, dryness, erythema, oiliness) and symptoms (e.g., burning, itching) of acne vulgaris were performed at all visits. The scale used for the Investigator's Static Global Assessment of facial acne vulgaris is shown in Table 7 below. The efficacy results are shown in Table 8 (Investigator's Static Global Assessment), Table 9 (percent reduction in inflammatory lesion counts), Table 10 (percent reduction in non-inflammatory lesion counts), and Table 11 (percent reduction in total lesion counts) below.

TABLE 7

Investigator's Static Global Assessment Scale of Facial Acne Vulgaris.

| Score | Definition |
| --- | --- |
| Grade 0 | Normal, clear skin with no evidence of acne vulgaris |
| Grade 1 | Skin almost clear: rare non-inflammatory lesions present, with rare non-inflamed papules (papules must be resolving and may be hyper-pigmented, though not pink-red) requiring no further treatment in the Investigator's opinion |
| Grade 2 | Some non-inflammatory lesions are present, with few inflammatory lesions (papules/pustules only, no nodulo-cystic lesions) |
| Grade 3 | Non-inflammatory lesions predominate, with multiple inflammatory lesions evident: several to many comedones and papules/pustules, and there may or may not be 1 small nodulo-cystic lesion |
| Grade 4 | Inflammatory lesions are more apparent: many comedones and papules/pustules, and there may or may not be a few nodulo-cystic lesions |
| Grade 5 | Highly inflammatory lesions predominate: variable number of comedones, many papules/pustules and nodulo-cystic lesions |

TABLE 8

Investigator's Static Global Assessment: Subjects with Success at Week 12.

| | Clindamycin Foam | Clindagel ™ | Vehicle Foam | Vehicle Gel |
| --- | --- | --- | --- | --- |
| Number of Subjects | 386 | 385 | 127 | 128 |
| Success | 120 (31%) | 105 (27%) | 23 (18%) | 26 (20%) |
| Confidence Limit[1] | | −2.60%, 10.23% | | |
| P-value[2] | | | | 0.0025 |

Note:

Success is defined as the proportion of subjects who have an Investigator's Static Global Assessment score of 0 or 1 at Week 12 (or end of treatment).

[1]Two-sided 95% confidence interval for the difference in success rate between Clindamycin Foam and Clindagel ™.

[2]P-value is derived from Cochran-Mantel-Haenszel test ($\alpha = 0.05$) stratified by site and compares Clindamycin Foam against Vehicle Foam.

Breslow-Day Test for Homogeneity of the by-site Odds Ratios for Clindamycin Foam versus Clindagel ™ Treatment Success: p = 0.9445, for Clindamycin Foam versus Vehicle Foam p = 0.6505

TABLE 9

Percent Reduction in Inflammatory Lesion Counts from Baseline to Week 12.

| | Clindamycin Foam | Clindagel ™ | Vehicle Foam | Vehicle Gel |
| --- | --- | --- | --- | --- |
| Number of Subjects | 386 | 385 | 127 | 128 |
| Percent Reduction from Baseline | | | | |
| n | 385 | 384 | 127 | 128 |
| mean (std) | 49.0(37.1) | 45.0(37.6) | 34.7(37.5) | 36.6(40.5) |
| median | 57.9 | 50.0 | 40.5 | 45.9 |

TABLE 9-continued

Percent Reduction in Inflammatory Lesion Counts from Baseline to Week 12.

|  | Clindamycin Foam | Clindagel ™ | Vehicle Foam | Vehicle Gel |
|---|---|---|---|---|
| min, max | (−93, 100) | (−135, 100) | (−112, 100) | (−111, 96) |
| confidence limit[1] |  | −0.97%, 9.17% |  |  |
| p-value[2] |  | 0.1096 | 0.0001 |  |
|  |  | 0.0478 | <.0001 |  |

[1]Two-sided 95% confidence interval for the difference in mean percent reduction between Clindamycin Foam and Clindagel ™. Treatment-by-site interaction: p = 0.7291.
[2]P-values are derived from a parametric ANOVA model (top) and a rank-transformed model (bottom) (α = 0.05) with terms for treatment and site and compare Clindamycin Foam against Clindagel ™ and Vehicle Foam, respectively.

TABLE 10

Percent Reduction in Non-Inflammatory Lesion Counts from Baseline to Week 12.

|  | Clindamycin Foam | Clindagel ™ | Vehicle Foam | Vehicle Gel |
|---|---|---|---|---|
| Number of Subjects | 386 | 385 | 127 | 128 |
| Percent Reduction from Baseline |  |  |  |  |
| n | 386 | 384 | 127 | 128 |
| mean (std) | 38.3(31.7) | 30.2(38.8) | 27.1(38.4) | 20.8(45.8) |
| median | 41.3 | 33.3 | 31.0 | 26.3 |
| min, max | (−82, 100) | (−183, 100) | (−192, 90) | (−200, 100) |
| confidence limit[1] |  | 3.25%, 13.03% |  |  |
| p-value[2] |  | 0.0013 | 0.0018 |  |
|  |  | 0.0037 | 0.0038 |  |

[1]Two-sided 95% confidence interval for the difference in mean percent reduction between Clindamycin Foam and Clindagel ™. Treatment-by-site interaction: p = 0.6922.
[2]P-values are derived from a parametric ANOVA model (top) and a rank-transformed model (bottom) (α = 0.05) with terms for treatment and site and compare Clindamycin Foam against Clindagel ™ and Vehicle Foam, respectively.

TABLE 11

Percent Reduction in Total Lesion Counts from Baseline to Week 12.

|  | Clindamycin Foam | Clindagel ™ | Vehicle Foam | Vehicle Gel |
|---|---|---|---|---|
| Number of Subjects | 386 | 385 | 127 | 128 |
| Percent Reduction from Baseline |  |  |  |  |
| n | 385 | 384 | 127 | 128 |
| mean (std) | 42.8(27.5) | 35.7(31.6) | 30.5(29.6) | 27.6(34.4) |
| median | 45.7 | 39.9 | 33.7 | 34.0 |
| min, max | (−43, 100) | (−93, 100) | (−87, 85) | (−77, 91) |
| confidence limit[1] |  | 3.03%, 11.20% |  |  |
| p-value[2] |  | 0.0007 | <.0001 |  |
|  |  | 0.0014 | <.0001 |  |

[1]Two-sided 95% confidence interval for the difference in mean percent reduction between Clindamycin Foam and Clindagel ™. Treatment-by-site interaction: p = 0.6782.
[2]P-values are derived from a parametric ANOVA model (top) and a rank-transformed model (bottom) (α = 0.05) with terms for treatment and site and compare Clindamycin Foam against Clindagel ™ and Vehicle Foam, respectively.

Of the 1026 subjects enrolled in the study, 54% were female and 46% were male. The majority of the subjects were Caucasian (64%) and the average age was 18.9 years (range from 12-55 years). There was an even distribution of age in the study, with 50% (516/1026) in the 12-16 year old age group and 50% (510/1026) in the age group of 17 years or older. Lesion counts (total, inflammatory and non-inflammatory) were similar across all treatment groups at Baseline. Overall, the majority of subjects (54%; 549/1026) had an Investigator's Static Global Assessment score of 3 at Baseline, with similar distribution across the treatment groups. There were no significant differences in the demographic or disease characteristics of the treatment groups at Baseline.

As the efficacy study results show (see, Tables 8-11), the clindamycin phosphate foam composition of the present invention is statistically superior in clinical efficacy to 1% clindamycin phosphate gel based on mean percent reduction for all three lesion counts (total, inflammatory, and non-inflammatory) and is statistically superior to the vehicle foam based on mean percent reduction for all three lesion counts (total, inflammatory, and non-inflammatory) and treatment success based on the Investigator's Static Global Assessment at the end of treatment.

The clindamycin phosphate foam composition of the present invention was also very well-tolerated. The most commonly reported dermal adverse event was application site burning: 6% (24/386) of subjects in the Clindamycin Foam group; 1% (3/385) of subjects in the Clindagel™ group; 7% (9/127) of subjects in the Vehicle Foam group; and 2% (2/128) of subjects in the Vehicle Gel group. However, these events were mild or moderate, intermittent in nature, and well-tolerated by the subjects in the study. All other application site reactions reported with Clindamycin Foam, including pruritus and dryness, occurred in <2% of subjects.

Example 8

This example shows a study on the comparative absorption of a clindamycin phosphate foam formulation versus a once-daily clindamycin phosphate topical gel formulation.

Methods:

The pharmacokinetic absorption profile of a clindamycin phosphate 1% foam formulation (Clindamycin Foam) was compared to that of a clindamycin phosphate 1% gel formulation (Clindamycin Gel). This study was a single center, randomized, open-label study of male and female subjects, 12 years of age or older, with mild to moderate acne vulgaris. For each treatment, Clindamycin Foam or Clindamycin Gel was administered once a day in the morning for 5 days. Subjects applied 4 grams of study medication to the face, neck, upper chest, and upper back at every treatment application. Evaluation of absorption occurred on the fifth day of treatment and included plasma and urine determination of clindamycin collected over a 12-hour period following application of the last dose. Plasma samples were obtained predose (i.e., prior to initiation of study drug treatment) on Day 1 of treatment and on Day 5 within 30 minutes prior to treatment application and at 1, 2, 4, 8, and 12 hours following treatment application. Urine was collected for 12 hours at Day 5 for determination of excretion of clindamycin. Treatment tolerability was assessed by reported adverse experiences.

Demographics:

Twenty-four subjects were enrolled and randomized to receive one of the two treatments (22 subjects were caucasian, 1 was black, and 1 was hispanic). The mean age of the subjects was 19 years (range: 13-46 years), the mean height was 66.9 inches (range: 62-71 inches), and the mean weight was 146.1 pounds (range: 113-185 pounds).

Figure 6:
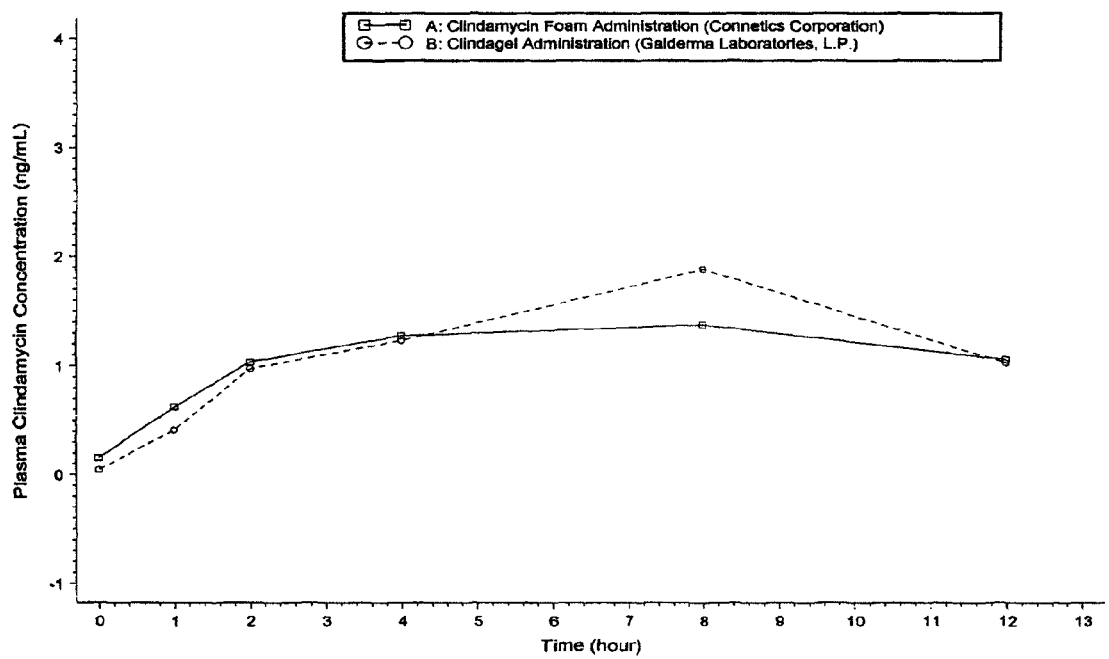
FIG. 6 shows plasma clindamycin concentration as a function of time after application of clindamycin foam and ClindaGel™.

Pharmacokinetic Results:

Clindamycin concentrations were detectable in 11 of the 12 subjects following Clindamycin Foam administration and in all 12 subjects following Clindamycin Gel administration. Overall, the mean $C_{max}$ and $AUC_{(0-12)}$ values were lower for Clindamycin Foam compared to Clindamycin Gel, with a 25% lower mean $C_{max}$ and a 9% lower $AUC_{(0-12)}$; the mean $T_{max}$ values were similar between the 2 treatments (see, Table 12 and FIG. 6). The fraction of clindamycin dose excreted in urine was marginal following both treatments, at 0.24% following Clindamycin Foam application compared to 0.30% following Clindamycin Gel application.

TABLE 12

Pharmacokinetic Parameters for Clindamycin (Plasma Clindamycin Concentration)

| Pharmacokinetic Parameters | Clindamycin Foam | | Clindamycin Gel | |
|---|---|---|---|---|
| | Arithmetic Mean | SD | Arithmetic Mean | SD |
| $C_{max}$ (ng/mL) | 1.562 | 0.813 | 2.075 | 1.239 |
| $T_{max}$ (hr) | 6.18 | 2.08 | 6.66 | 2.46 |
| $AUC_{(0-12)}$ (ng-hr/mL) | 13.69 | 6.248 | 15.12 | 10.26 |

Safety:

Few adverse events were reported during the study, with only 4 of 24 subjects reporting a total of four adverse events between the time subjects initiated study treatment and completion of the study. Two subjects assigned to treatment with Clindamycin Foam reported one adverse event each (i.e., application site dryness and headache NOS) and two subjects assigned to Clindamycin Gel reported one adverse event each (i.e., blister and dizziness). Most adverse events were mild in severity and were considered to be unrelated to the study drug treatment; only the report of dryness at the application site was probably related to study drug treatment. There were no deaths, serious adverse experiences, episodes of diarrhea, or other significant adverse experiences and no subjects discontinued the study prior to completion of all blood draws on Day 5 (study termination).

Conclusions:

The extent of clindamycin absorption following Clindamycin Foam administration was lower, but comparable to that following Clindamycin Gel administration. The mean $C_{max}$ and mean $AUC_{(0-12)}$ values in plasma on Day 5 were 25% and 9% lower, respectively, following the Clindamycin Foam treatment compared to Clindamycin Gel treatment. The amount of clindamycin excreted in urine during the first 12-hours post-dose was 21% lower for the Clindamycin Foam treatment group. Clindamycin Foam administered topically for 5 consecutive days in 4 gram doses appeared to be safe and well-tolerated by the subjects.

Example 9

This example shows a comparative study on the skin penetration of various clindamycin phosphate formulations in vitro using a human skin model system.

Summary

The purpose of the study was: (1) to quantify the in vitro percutaneous absorption of clindamycin; and (2) to characterize clindamycin distribution in different skin compartments, following the application of (1) a 1% clindamycin phosphate foam formulation of the present invention (Foam); (2) a 1% ClindaGel™ topical gel formulation (Gel); and (3) a 1% Cleocin T® solution formulation (Solution), in dermatomed human skin using the finite dose technique and In-Line Diffusion Cells.

Methods:

The formulations (Foam, Gel, and Solution) were tested for percutaneous absorption of clindamycin on skin sections from three different skin donors. The skin sections were dosed for 24 hours, during which the dermal receptor solution was collected every 4 hours and saved for subsequent analysis. At the end of the dosing period, the surface of the skin was washed and the skin was split into epidermis and dermis. The wash from the surface of the skin, the epidermis, the dermis, and samples of the receptor fluid were then analyzed for clindamycin using high performance liquid chromatography coupled with mass spectrometry (LC/MS).

Results:

At the end of the 24-hour dosing period, the Solution formulation contained the highest amount of clindamycin in the receptor fluid, followed by the Foam formulation and lastly the Gel formulation (see, Table 13, below). As shown in Table 13, there was no significant difference (p>0.1) in the cumulative amount of clindamycin in the receptor fluid from Foam and Solution formulations at 24 hours after dosing. At that time point, both Foam and Solution formulations delivered more clindamycin into receptor fluid than the Gel formulation (p<0.1). Similar amounts of clindamycin were found in the epidermis from all formulations. However, the Gel formulation resulted in a higher amount of clindamycin in the dermis than the Foam and Solution formulations. Both the Foam and Solution formulations resulted in similar amounts of clindamycin in the dermis.

TABLE 13

Clindamycin in Receptor Fluid and Skin at 24 Hours After Dosing (Mean ± Std. Error)

| | Formulation | | |
|---|---|---|---|
| Distribution | Foam (n = 3 × 3) | Gel (n = 3 × 3) | Solution (n = 3 × 3) |
| In Receptor Fluid | 0.16% ± 0.02% | 0.05% ± 0.04% | 0.39% ± 0.16% |
| In Dermis | 3.08% ± 0.71% | 5.45% ± 1.33% | 3.33% ± 0.83% |
| In Epidermis | 5.35% ± 0.69% | 5.48% ± 1.25% | 5.78% ± 1.54% |

The flux profiles of the three formulations were very similar in form, with the maximum rate achieved already in the first time point (i.e., between 0 to 4 hours after application) and decreasing steadily thereafter. The highest maximum rate was produced from the Solution formulation, followed by the Foam and lastly from the Gel formulation.

Conclusion:

The Foam formulation delivered clindamycin with a profile similar to that of the Solution formulation, which produced the highest delivery of clindamycin in the current in vitro skin permeation study. The amount of clindamycin in the epidermis, dermis, and receptor fluid was very similar and exhibited no significant differences between the Foam and the Solution formulations.

Example 10

Introduction

The 1% clindamycin Foam formulation is suitable as a topical treatment for acne. In contrast to products currently available on the market, the Foam formulation provides for elegant, rapid, and non-staining drug delivery, leaving very little residue on the skin. The current study investigated and compared the delivery, skin permeation profile, and drug distribution in the skin of clindamycin from Foam, Gel, and Solution formulations.

The in vitro human skin penetration model has proven to be a valuable tool for the study of percutaneous absorption and the determination of the pharmacokinetics of topically applied drugs. This method has historic precedent for accurately predicting in vivo percutaneous absorption kinetics. The model uses excised human skin mounted in specially designed diffusion chambers or cells that allow the skin to be maintained at a temperature and humidity that match typical in vivo conditions. A finite dose (e.g., 4-6 mg/cm$^2$) of the formulation is applied to the outer surface of the skin and drug absorption is measured by monitoring its rate of appearance in the receptor solution bathing the inner surface of the skin. Skin content can be determined by extraction and analysis of the drug from different skin layers. As such, data defining total absorption, rate of absorption, and drug distribution in the skin and on its surface can be accurately determined using this model.

Deviations

One cell (1G) did not pass the skin integrity test, and was used instead as an untreated control. None of the other cells was excluded from the results.

Test Articles

Analytical standards were obtained from Sigma Chemicals and United States Pharmacopeia (USP).

The tested formulations were as follows:
1. Foam: 1% clindamycin phosphate foam of the present invention; Manufacturer's lot no. SEAX-C.
2. Gel: 1% Clindagel topical gel (clindamycin phosphate topical gel equivalent to 1% clindamycin; Galderma Laboratories, L.P., Fort Worth, Tex.); Manufacturer's lot no. RFDA.
3. Solution: 1% Cleocin T® Solution (clindamycin phosphate topical solution, USP; equivalent to 1% (10 mg/mL) clindamycin; Pharmacia & Upjohn Company, Kalamazoo, Mich.); Manufacturer's lot no. 89FTK.

Methods and Procedures

Methodology:

Percutaneous absorption was measured using the in vitro skin finite dose technique. Human abdomen skin without obvious signs of skin disease, obtained from cosmetical surgery, was used in this study. The skin samples were dermatomed to approximately 0.25 mm, sealed in a water-impermeable container, and stored at ~−80° C. until the day of the experiment. Prior to use, the skin samples were thawed by exposing the container to ambient temperature.

Skin from a single donor was cut into multiple smaller sections, but remained large enough to fit on an 0.64 cm$^2$ exposure area of In-Line diffusion cells (Permegear Inc., Bethlehem, Pa.). The dermal chamber was filled to capacity with a receptor solution of 10-times diluted phosphate-buffered isotonic saline (PBS), pH 7.4±0.2, and the epidermal chamber was left open to the ambient laboratory environment. The cells were then placed in a cell warmer support in which the temperature of the dermal chamber was maintained at 37° C.±0.2° C.

To assure the integrity of each skin section, its permeability to tritiated water was determined before application of the test formulations (Franz et al., *Abst. J. Invest. Derm.*, 94:525 (1990)). Following a brief (0.5-1 hour) equilibrium period, 100 μL of $^3H_2O$ (Moravek, Calif., sp. Act. ~5 μCi/mL) was layered across the top of the skin using a pipette so that the entire exposed surface was covered. After 5 minutes, the $^3H_2O$ aqueous layer was removed. At 30 minutes, the receptor solution was collected and analyzed for radioactive content by liquid scintillation counting. Skin specimens in which penetration of $^3H_2O$ was less than 1.75% applied dose were considered acceptable.

Dosing and Sampling:

The Foam formulation was first dispensed as foam into a 20-mL vial and warmed to 37° C. in a water bath to thoroughly liquefy the foam. All formulations were then applied to the skin sections using a positive displacement pipette set to deliver 5 μL. Each test formulation was applied to three replicate sections of the same donor skin at a target dose of 5 μL/0.64 cm$^2$. The dose was spread over the entire surface with the tip of the pipette. The skin sections were dosed for 24 hours, during which the dermal receptor solution was collected every 4 hours and saved for analysis. A spare chamber was used with untreated skin to test for any interfering substances during the analytical assay.

At the end of the 24-hour dosing period, following the last receptor solution sample collection, the skin surface was washed by applying 50 μL of acetonitrile, wiped with a pre-cut tissue paper twice consecutively, and stripped with a transparent tape twice consecutively. The tissue paper and tape were placed in a vial. The skin was placed on a 50° C. heat block for 1.5 minutes, then the epidermis was carefully peeled off the skin and placed in one vial, while the remaining piece of skin (dermis) was placed into another vial. To each of these three vials, 5 mL of acetonitrile was added to extract the drug from the samples.

Preparation of Samples:

Clindamycin was extracted from the receptor solutions by running 3.0 mL of the samples (with 200 μL addition of an internal standard: lincomycin hydrochloride) through solid phase extraction (C18 SPE cartridges) and eluting the clindamycin using 0.5 mL methanol. After vortexing, 100 μL of solution was placed into HPLC vials containing 900 μL of Milli-Q purified water and mixed well before analysis. From the acetonitrile based samples, 100 μL of solution was mixed with 1004 of internal standard solution in test tubes. After the addition of 800 μL Milli-Q water, the tubes were centrifuged and the supernatant was transferred into HPLC vials for analysis.

Analytical Methods:

Quantification of clindamycin was performed by high performance liquid chromatography combined with mass spectrometry (LC/MS/MS) on a Micromass LC/MS/MS system. The mobile phase consisting of acetonitrile, methanol, water, and formic acid (33%:33%:33%:0.1%) was pumped through a Keystone Aquasil C18 column (1.0×30 mm, 3μ) at ambient temperature at a flow rate of 0.05 mL/min. (5 minute run duration). Forty microliters of sample were injected. Eluting peaks were monitored at the M/Z of 425>126 Da. Peak areas were quantified to concentration using an external standard of clindamycin hydrochloride correlated to an internal standard lincomycin hydrochloride.

Pivotal Study Details:

This study was designed to assess the effects of different formulations on clindamycin percutaneous absorption. Three skin donor samples, each cut into 9-10 replicate sections, were prepared and mounted onto chambers. Receptor solution samples were collected at 4-hour time intervals, up to 24 hours post-application. The receptor solution used throughout was PBS (i.e., 1 mM phosphate buffer solution, pH 7.4 at 25° C.; BioChemika). Extracts from the surface wash, epidermis, and dermis were analyzed to obtain the mass balance of the applied drug. Data for the different formulations were compared and evaluated for statistical differences using a Student-t test for multiple comparisons.
Results

TABLE 14

Skin Integrity Test Results.

| Donor ID | Sex | Integrity Test Results* | |
|---|---|---|---|
| 2003.001 | Female | 0.05 ± 0.02 | Pass** |
| 2003.002 | Female | 0.04 ± 0.05 | Pass |
| 2003.003 | Female | 0.03 ± 0.02 | Pass |

*Results are reported as % applied $^3H_2O$ ± standard deviation; Acceptance: <1.75%. All skin samples were obtained from abdominoplastic surgeries. Donor age is unknown.
**Excluding 1 cell that failed the test.

Figure 7:
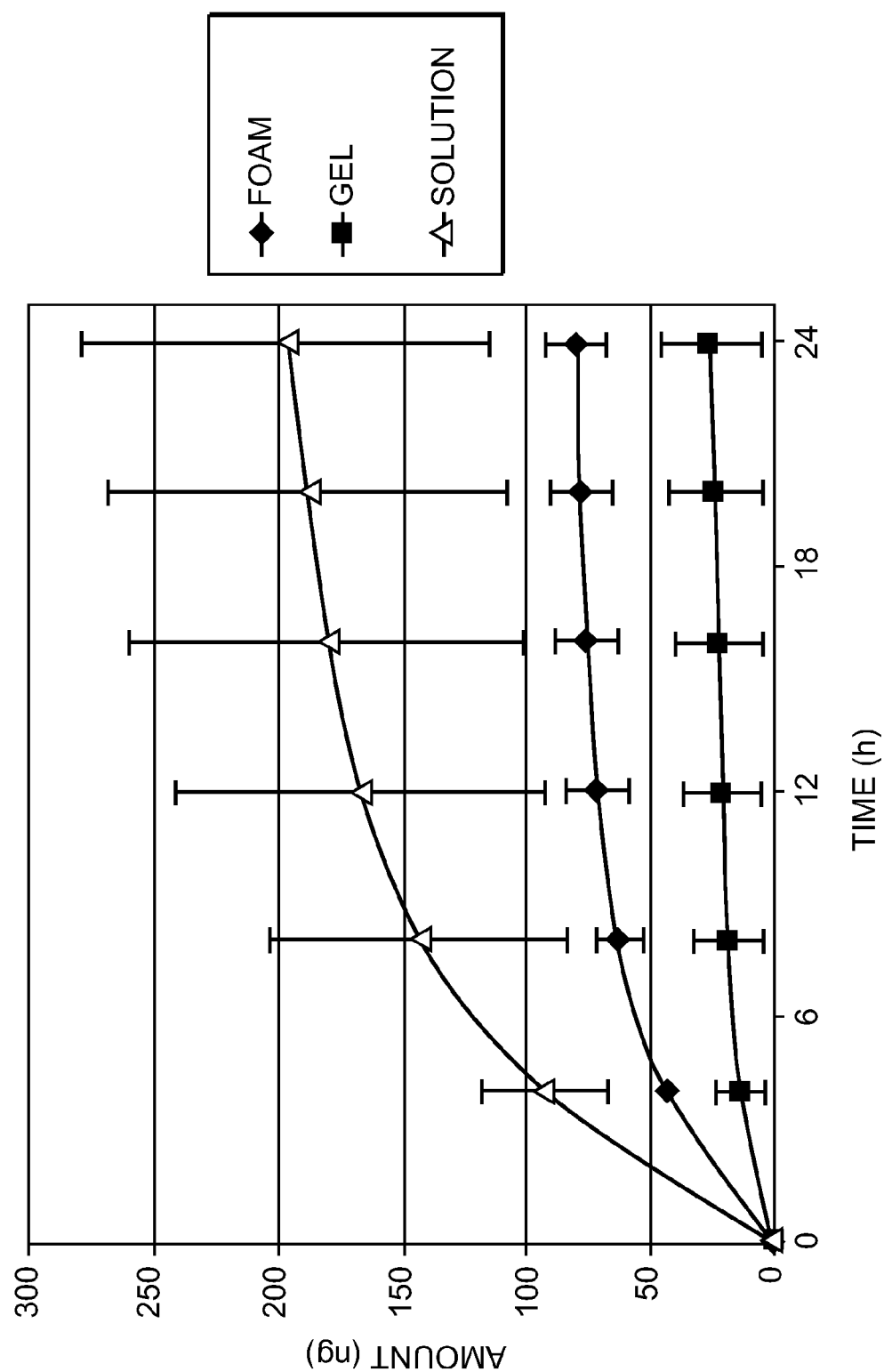
FIG. 7 shows a graph of the cumulative percutaneous absorption of clindamycin foam, ClindaGel™, and Cleocin T® solution over a 24-hour period. Each time-point represents the mean total absorption±standard error for 3 skin donors (3 replicates for each). *$p<0.05$ (gel vs. foam); $p<0.06$ (gel vs. solution); $p>0.1$ (foam vs. solution).
Figure 8:
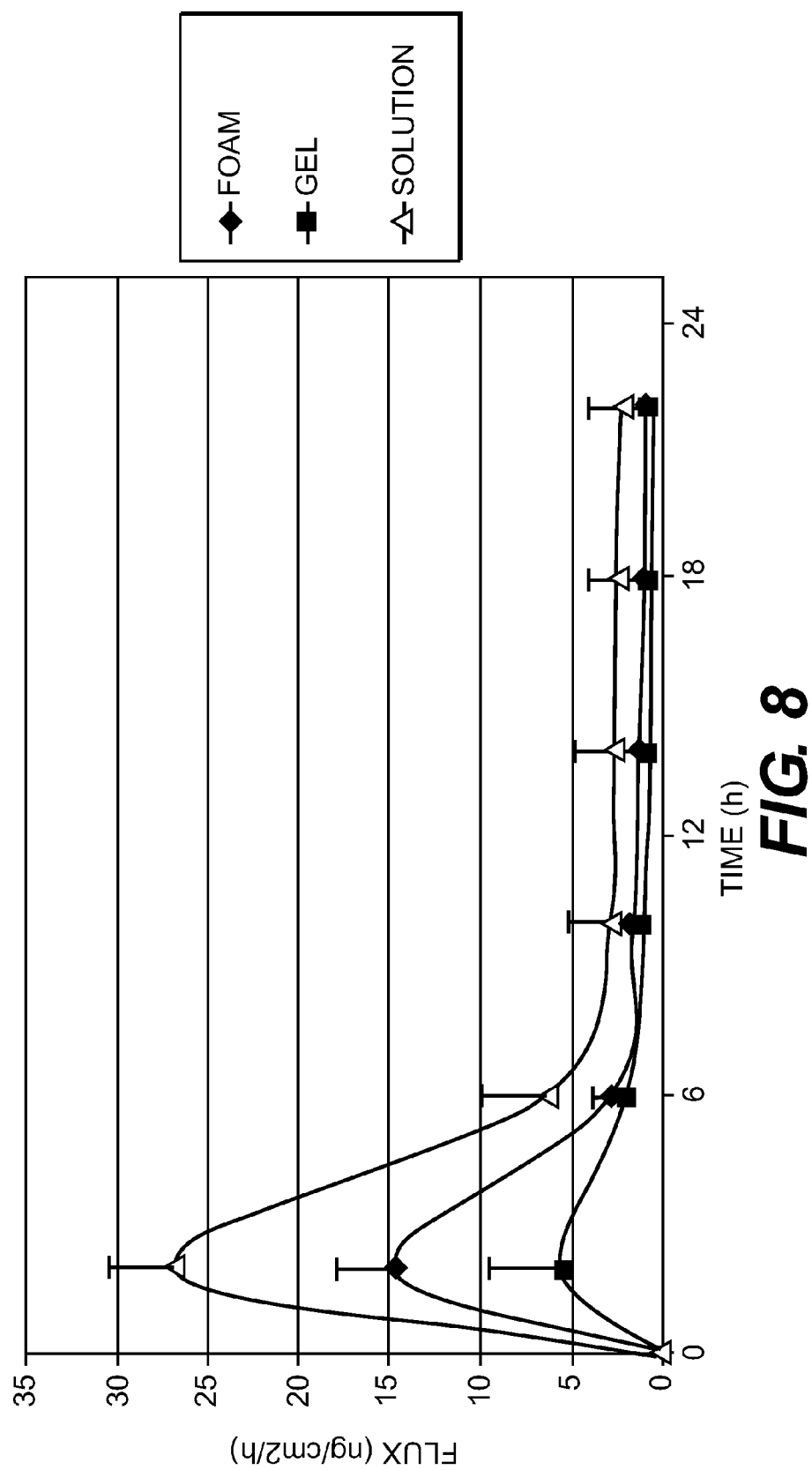
FIG. 8 shows a graph of the flux profile for the percutaneous absorption of clindamycin foam, ClindaGel™, and Cleocin T® solution over a 24-hour period. Each time-point represents the mean absorption±standard error for 3 skin donors (3 replicates for each).
Figure 9:
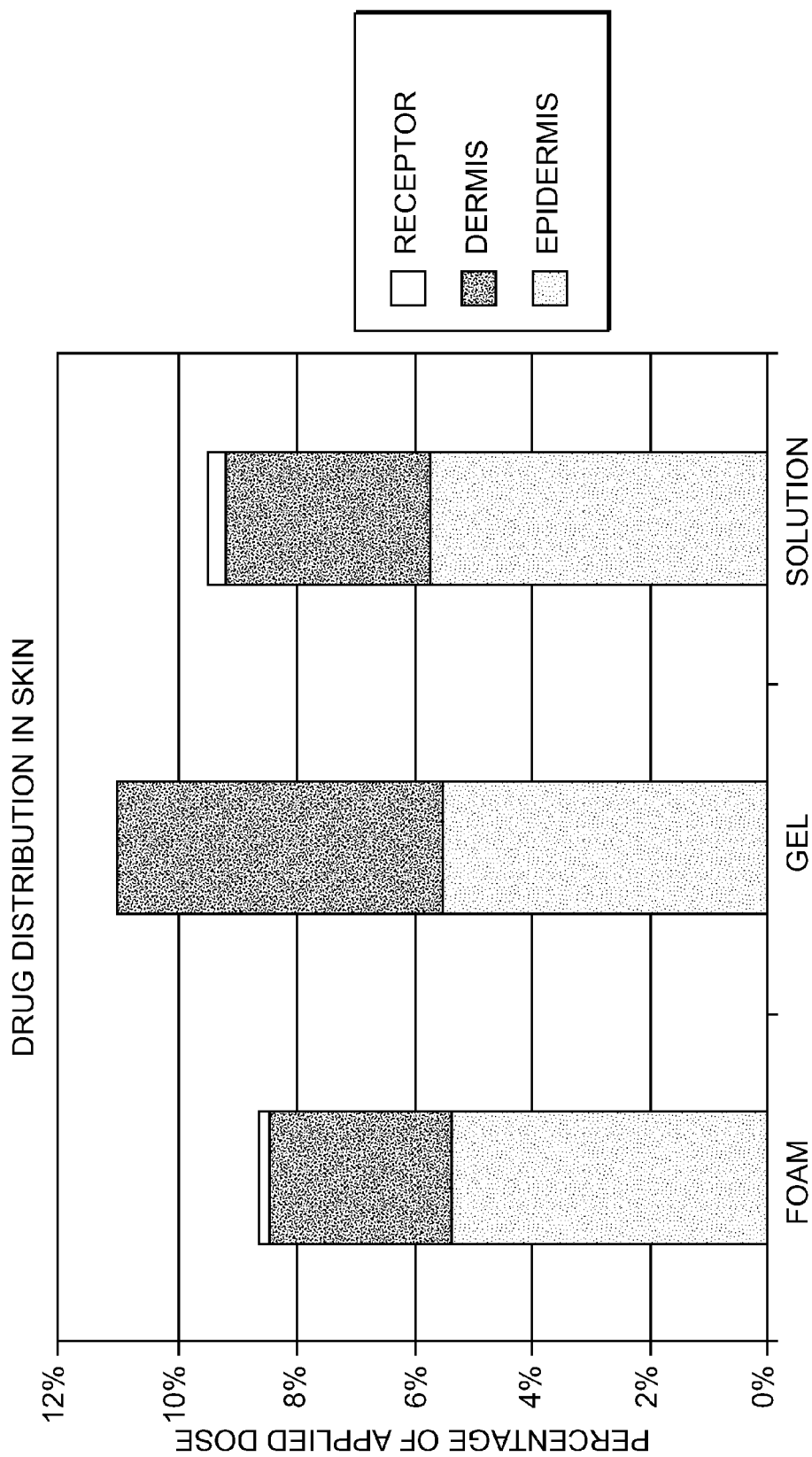
FIG. 9 shows a graph of the distribution of clindamycin in different layers of the skin 24 hours after application of clindamycin foam, ClindaGel™, and Cleocin T® solution.

Drug Content and Distribution:

The results for the mean percutaneous absorption of clindamycin in the tested formulations are summarized graphically in FIG. 7 as the cumulative penetrated amount (i.e., mean total absorption) in 24 hours and in FIG. 8 as the flux profile for a 24-hour period. The numerical data are presented in Table 15 below. FIG. 9 shows the distribution of clindamycin in different skin layers.

TABLE 15

Clindamycin Distribution on Skin Surface, in Skin Layers, and in Receptor Fluid at 24 Hours After Dosing (Mean ± Standard Error).

| Distribution | Foam (n = 3 × 3) | Gel (n = 3 × 3) | Solution (n = 3 × 3) |
|---|---|---|---|
| In Receptor Fluid | 0.16% ± 0.02% | 0.05% ± 0.04% | 0.39% ± 0.16% |
| In Dermis | 3.08% ± 0.71% | 5.45% ± 1.33% | 3.33% ± 0.83% |
| In Epidermis | 5.35% ± 0.69% | 5.48% ± 1.25% | 5.78% ± 1.54% |
| In Surface Wash | 2.77% ± 0.39% | 20.72% ± 1.59% | 6.56% ± 1.12% |
| Total Recovery | 11.37% | 31.70% | 16.06% |

In FIG. 7, the cumulative amount of clindamycin that penetrated through the skin over 24 hours increased sharply for all formulations already in the first time point, gradually reaching a plateau towards 24 hours. The Solution formulation delivered the most clindamycin, followed by the Foam formulation, and lastly the Gel formulation. Both Solution and Foam formulations delivered significantly more clindamycin into the receptor fluid than the Gel formulation (p<0.06 and p<0.05, respectively) up to the 24-hour time point. There was no significant difference (p>0.1) in the cumulative amount of clindamycin in the receptor fluid up to 24 hours from Foam and Solution formulations.

This can further be observed from the flux profile. The flux plots in FIG. 8 show that the maximum rate of delivery was achieved in the first time point (0 to 4 hours after application) for all formulations, and decreased steadily thereafter. The flux profiles of the three formulations were very similar in form. The highest maximum rate was produced from the Solution formulation, followed by the Foam formulation, and lastly from the Gel formulation.

Similar amounts of clindamycin were found in the epidermis for all formulations. Although the Gel formulation resulted in a higher amount of clindamycin in the dermis, both Foam and Solution formulations resulted in similar amounts of clindamycin in the dermis.

The amount recovered from the wash was very low, due to the high affinity of clindamycin to the adhesive material in the tape, which was filtered during sample preparation.

The mass balance of the experiments is also presented in Table 15.

Conclusions

Data from this study demonstrated that:
1. The Foam vehicle facilitates a higher level of clindamycin delivery across the skin than the Gel formulation, but a lower level than the Solution formulation;
2. The maximum flux rate was achieved shortly after application of all formulations, with the order of magnitude from highest to lowest being: Solution>Foam>Gel; and
3. The skin distribution at 24 hours showed an equal amount of clindamycin in the epidermis for all formulations and a slightly higher amount in the dermis for the Gel formulation compared to the Foam and Solution formulations.

Thus, this study shows that the clindamycin phosphate foam formulation of the present invention is superior to a clindamycin gel formulation for enhanced delivery of clindamycin across the skin at a higher flux rate. Further, unlike a clindamycin solution formulation, the clindamycin phosphate foam formulation of the present invention does not readily run off the site of application, providing for the administration of a more controlled amount of clindamycin.

Example 11

This example illustrates non-alcoholic and alcoholic foam compositions of the present invention comprising a combination of clindamycin phosphate and tretinoin.

| | NON-ALCOHOLIC CLINDAMYCIN/TRETINOIN FOAM | | |
|---|---|---|---|
| ITEM | INGREDIENT | % w/w (without propellant) | % w/w (with propellant) |
| 1 | Purified water | 86.90 | 82.545 |
| 2 | Propylene glycol | 7.50 | 7.13 |
| 3 | Disodium EDTA | 0.10 | 0.10 |
| 4 | Clindamycin phosphate | 1.255 | 1.191 |
| 5 | Laureth-4 | 2.00 | 1.90 |
| 6 | POE (15) glyceryl monolaurate | 2.00 | 1.90 |
| 7 | Butylated hydroxytoluene | 0.02 | 0.02 |
| 8 | Retinoic acid (tretinoin) | 0.025 | 0.024 |
| 9 | Methyl paraben | 0.20 | 0.19 |
| 10 | Aerosol Base (Items 1-9) | 100.00 | 95.00 |
| 11 | Hydrocarbon propellant | NIL | 5.00 |
| | Total | 100.00 | 100.00 |

Items 1-4 are added stepwise to mixing vessel A. Items 5-9 are added stepwise to mixing vessel B. Each phase is heated to approximately 60° C. While stirring, Phase B is added to Phase A, mixed until uniform, and cooled to 30° C. The Aerosol Base (Item 10) is then added to an aerosol can, and a valve is secured onto the aerosol can. A propellant (Item 11) is added to the aerosol package (i.e., aerosol can with valve containing Aerosol Base). The Aerosol Package is placed into a 55° C. water bath for 1-2 minutes, then shaken well and cooled to room temperature. The Aerosol Package is shaken immediately prior to dispensing.

ALCOHOLIC CLINDAMYCIN/TRETINOIN FOAM

| ITEM | INGREDIENT | % w/w (without propellant) | % w/w (with propellant) |
|---|---|---|---|
| 1 | Purified water | 81.90 | 77.795 |
| 2 | Ethanol | 5.00 | 4.75 |
| 3 | Propylene glycol | 7.50 | 7.13 |
| 4 | Disodium EDTA | 0.10 | 0.10 |
| 5 | Clindamycin phosphate | 1.255 | 1.191 |
| 6 | Laureth-4 | 2.00 | 1.90 |
| 7 | POE (15) glyceryl monolaurate | 2.00 | 1.90 |
| 8 | Butylated hydroxytoluene | 0.02 | 0.02 |
| 9 | Retinoic acid (tretinoin) | 0.025 | 0.024 |
| 10 | Methyl paraben | 0.20 | 0.19 |
| 11 | Aerosol Base (Items 1-10) | 100.00 | 95.00 |
| 12 | Hydrocarbon propellant | NIL | 5.00 |
|  | Total | 100.00 | 100.00 |

Items 1-5 are added stepwise to mixing vessel A. Items 6-10 are added stepwise to mixing vessel B. While stirring, Phase B is added to Phase A and mixed until uniform. The Aerosol Base (Item 11) is added to an aerosol can and a valve is secured onto the aerosol can. A propellant (Item 12) is added to the Aerosol Package (i.e., aerosol can with valve containing Aerosol Base). The Aerosol Package is placed into a 55° C. water bath for 1-2 minutes, then shaken well and cooled to room temperature. The Aerosol Package is shaken immediately prior to dispensing.

Example 12

This example illustrates non-alcoholic and alcoholic foam compositions of the present invention comprising a combination of clindamycin phosphate and benzoyl peroxide.

NON-ALCOHOLIC CLINDAMYCIN/BENZOYL PEROXIDE FOAM

| ITEM | INGREDIENT | % w/w (without propellant) | % w/w (with propellant) |
|---|---|---|---|
| 1 | Purified water | 86.39 | 82.07 |
| 2 | Disodium EDTA | 0.50 | 0.47 |
| 3 | Clindamycin phosphate | 1.25 | 1.19 |
| 4 | Laureth-4 | 4.00 | 3.80 |
| 5 | Methyl paraben | 0.20 | 0.19 |
| 6 | Benzoyl Peroxide (75%) | 6.66 | 6.33 |
| 7 | Xanthan gum | 1.00 | 0.95 |
| 8 | Aerosol Base (Items 1-7) | 100.00 | 95.00 |
| 9 | Hydrocarbon propellant | NIL | 5.00 |
|  | Total | 100.00 | 100.00 |

ALCOHOLIC CLINDAMYCIN/BENZOYL PEROXIDE FOAM

| ITEM | INGREDIENT | % w/w (without propellant) | % w/w (with propellant) |
|---|---|---|---|
| 1 | Purified water | 76.38 | 72.56 |
| 2 | Ethanol | 10.00 | 9.50 |
| 3 | Disodium EDTA | 0.50 | 0.48 |
| 4 | Clindamycin phosphate | 1.25 | 1.19 |
| 5 | Laureth-4 | 4.00 | 3.80 |
| 6 | Methyl paraben | 0.20 | 0.19 |
| 7 | Benzoyl Peroxide (75%) | 6.67 | 6.33 |
| 8 | Xanthan gum | 1.00 | 0.95 |
| 9 | Aerosol Base (Items 1-8) | 100.00 | 95.00 |
| 10 | Hydrocarbon propellant | NIL | 5.00 |
|  | Total | 100.00 | 100.00 |

NON-ALCOHOLIC CLINDAMYCIN/BENZOYL PEROXIDE FOAM

| ITEM | INGREDIENT | % w/w (without propellant) | % w/w (with propellant) |
|---|---|---|---|
| 1 | Purified water | 79.72 | 75.73 |
| 2 | Disodium EDTA | 0.50 | 0.48 |
| 3 | Clindamycin phosphate | 1.25 | 1.19 |
| 4 | Laureth-4 | 4.00 | 3.80 |
| 5 | Methyl paraben | 0.20 | 0.19 |
| 6 | Benzoyl Peroxide (75%) | 13.33 | 12.66 |
| 7 | Xanthan gum | 1.00 | 0.95 |
| 8 | Aerosol Base (Items 1-7) | 100.00 | 95.00 |
| 9 | Hydrocarbon propellant | NIL | 5.00 |
|  | Total | 100.00 | 100.00 |

ALCOHOLIC CLINDAMYCIN/BENZOYL PEROXIDE FOAM

| ITEM | INGREDIENT | % w/w (without propellant) | % w/w (with propellant) |
|---|---|---|---|
| 1 | Purified water | 69.72 | 66.23 |
| 2 | Ethanol | 10.00 | 9.50 |
| 3 | Disodium EDTA | 0.50 | 0.48 |
| 4 | Clindamycin phosphate | 1.25 | 1.19 |
| 5 | Laureth-4 | 4.00 | 3.80 |
| 6 | Methyl paraben | 0.20 | 0.19 |
| 7 | Benzoyl Peroxide (75%) | 13.33 | 12.66 |
| 8 | Xanthan gum | 1.00 | 0.95 |
| 9 | Aerosol Base (Items 1-8) | 100.00 | 95.00 |
| 10 | Hydrocarbon propellant | NIL | 5.00 |
|  | Total | 100.00 | 100.00 |

Example 13

This example illustrates a large-scale production of the clindamycin phosphate foam compositions of the present invention.

Two mixing vessels were used for compounding and manufacturing. One stainless steel tank was used to prepare an ethanolic phase solution containing the excipients (cetyl alcohol, stearyl alcohol, polysorbate 60, and propylene glycol). A second stainless steel tank was used to prepare an aqueous solution of the active agent and potassium hydroxide. Water and ethanol were first dispensed into their respective tanks, weighed, and the components were then added. The solutions were mixed until each component had dissolved before adding the next. Both phases were then transferred to filling vessels. The aqueous phase was filtered through a 0.2 micron filter prior to transferring to the filling vessel. Each filling vessel was connected to a 10 micron filter prior to the filling ram on the filling line and delivery was controlled through a positive displacement diaphragm pump. An aliquot of each solution phase was independently dispensed into each can and the can was subsequently vacuum crimped and sealed. A metered amount of propellant was then injected via the valve to complete the formulation. Each can was then leak tested before final placement of the actuator and cap, inkjet labeling, and secondary packaging.

As noted above, separate preparations of an ethanolic solution and an aqueous solution were used for the preparation of the clindamycin phosphate foam composition. Ethanol is used for rapid and complete dissolution of cetyl alcohol and stearyl alcohol, which have low water solubility. Polysorbate 60 and propylene glycol are liquids that are miscible in ethanol and water. The active compound is a dry solid and dissolves readily in water. The potassium hydroxide solution is added to adjust the pH.

Example 14

This example describes a foam quality rating scale and a range of experiments that can be conducted to characterize foam products in a qualitative and quantitative manner.

In this particular example, foams are rated according to the observable physical characteristics, such as a visual aid, of foam samples:
1. Liquid—characterized as being a low viscosity fluid that readily flows away from the dispensing area when dispensed. "Liquid" may additionally have the presence of minute bubbles and as such would have an appearance similar to a carbonated beverage. Typically, "Liquid" would have similar flow properties to a sample of water or milk dispensed on to a similar substrate.
2. Runny Foam—characterized as being a three-dimensional, semi-solid foam structure that readily flows away from the dispensing area when dispensed. Generally, "Runny Foam" has a relatively large bubble size and is typically less than 10 mm in diameter. Typically, "Runny Foam" would exhibit similar flow characteristics to foam on the top of a milkshake.
3. Soft Foam—characterized as being a three-dimensional, semi-solid foam structure that does not readily flow away from the dispensing area when dispensed. Generally, "Soft Foam" has a relatively large bubble size and is typically less than 5 mm in diameter. Typically, "Soft Foam" would exhibit similar flow characteristics to whipped egg whites.
4. Creamy Foam—characterized as being a three-dimensional, semi-solid foam structure that does not readily flow away from the dispensing area when dispensed. Generally, "Creamy Foam" has a relatively small bubble size and is typically much less than 1 mm in diameter. Typically, "Creamy Foam" would exhibit similar flow characteristics to whipped cream/shaving cream.
5. Crisp Foam—characterized as being a three-dimensional, semi-solid foam structure that does not readily flow away from the dispensing area when dispensed. Generally, "Crisp Foam" has a relatively small bubble size and is typically much less than 1 mm in diameter. Typically, "Crisp Foam" would exhibit similar flow characteristics to a loosely packed snowball and would exhibit similar tensile properties such as being brittle (i.e., can be readily pulled apart) and have substantially "solid characteristics."

General physical appearance of the foam is described using the foam rating scale over a range of temperatures.

Bubble size and average bubble size are measured visually with a suitable reference measurement scale over a range of temperatures. Techniques include: (i) visual, e.g., estimating bubble size relative to a metric scale; and (ii) microscopic, e.g., estimating bubble size using a calibrated eyepiece graticule.

Foam viscosity is measured with a suitable viscosity measuring device. Techniques include: (i) Brookfield Synchro-lectric rotating spindle viscometer with Ultra-low viscosity adapter, where liquefied foam is introduced into the temperature-controlled device and viscosity is measured at a range of temperatures; and (ii) Brookfield Cone & Plate Viscometer, where samples of foam are introduced between the cone and plate and the rheology of the foam is determined over a range of shear rates and temperatures.

Foam density is measured with a suitable density determination apparatus. Techniques include: (i) pycnometer/ weight per gallon cup, where foam at fixed temperatures is carefully introduced into a fixed-volume vessel of known volume and mass; and (ii) Electronic density/specific gravity meter, where a slow stream of foam at fixed temperatures is introduced into a flow-through cell and the density is determined by the oscillating body method.

Foam expansion rate is the determination of the rate at which the foam expands. Suitable techniques for measuring the expansion rate include: (i) visual, where foam is introduced into a measuring cylinder and the occupied volume is recorded over time at a range of temperatures, (ii) visual/ timelapse photography, where the cross-sectional area/volume is estimated over a relatively short time-scale, and (iii) visual/rate of growth, where a fixed quantity of foam is introduced into a constant diameter capillary tube and the time at which the foam passes calibrated marks is recorded.

Product clarity is described by visual inspection of the product. This involves preparing formulations in transparent, plastic-coated glass aerosol vessels and storing the products in an incubator capable of controlled temperature storage over the range of from 0° C. to 30° C. The temperature is reduced (from the minimum storage temperature at which the product is clear) at a rate of approximately −1° C./day and the observations are recorded. Once the lowest temperature has been reached the temperature is increased at the rate of +1° C./day and the observations are recorded.

The "minimum use temperature" is the lowest recorded temperature (i.e., increasing temperature) where precipitated matter has redissolved.

Flow rate is a measurement of the flow characteristics. This technique involves dispensing foam at a range of temperatures onto a controlled-temperature surface on an incline (or perhaps by spraying onto a vertical surface) and the distance the liquid travels from the dispensing area and time taken are recorded.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

What is claimed is:

1. A topical delivery foam composition in a pressurized container, said composition consisting essentially of, with respect to the total weight of the composition:
   up to 15% w/w of at least one pharmaceutically active agent, wherein the at least one pharmaceutically active agent comprises a combination of benzoyl peroxide and clindamycin or a salt or ester thereof;
   from about 83% to about 97.9% w/w of an aqueous quick-breaking foaming agent consisting essentially of water, a surfactant, and a pH adjusting agent present in an amount sufficient to adjust the pH of the composition to between about 4.0 to about 6.5;
   and from about 2% to about 7% w/w of an aerosol propellant selected from the group consisting of a hydrocarbon, a chlorofluorocarbon, dimethyl ether, hydrofluorocarbons and a mixture thereof,
   wherein said composition is a quick-breaking foam after release from said container.

2. The topical delivery foam composition of claim 1, wherein said clindamycin is clindamycin phosphate.

3. The topical delivery foam composition of claim 1, wherein said surfactant is selected from the group consisting of a block co-polymer, fatty acid ethoxylates, fatty alcohol ethoxylates, polysorbates and glycerol ester ethoxylates.

4. The topical delivery foam composition of claim 1, wherein said surfactant is present in an amount of from about 0.1% to about 10% w/w.

5. The topical delivery foam composition of claim 4, wherein said surfactant is present in an amount of from about 0.1% to about 6% w/w.

6. The topical delivery foam composition of claim 1, wherein said pH adjusting agent is a buffer.

7. The topical delivery foam composition of claim 6, wherein said buffer is selected from the group consisting of citrate/citric acid, acetate/acetic acid, phosphate/phosphoric acid, formate/formic acid, propionate/propionic acid, lactate/lactic acid, carbonate/carbonic acid and ammonium/ammonia buffer.

8. The topical delivery foam composition of claim 1, wherein said aerosol propellant is a hydrocarbon propellant.

9. The topical delivery foam composition of claim 1, wherein the water is present in an amount of about 80% to about 95% w/w.

10. The topical delivery foam composition of claim 1, wherein said composition further comprises xanthan gum.

11. A topical delivery foam composition in a pressurized container, said composition consisting essentially of:
    benzoyl peroxide and clindamycin or a salt or ester thereof;
    an aqueous quick-breaking foaming agent consisting essentially of:
    a) water,
    b) a surfactant, and
    c) a pH adjusting agent present in an amount sufficient to adjust the pH of the composition to between about 4.0 to about 6.5; and
    an aerosol propellant selected from the group consisting of a hydrocarbon, a chlorofluorocarbon, dimethyl ether, hydrofluorocarbons and a mixture thereof,
    wherein said composition is a quick-breaking foam after release from said container.

12. The topical delivery foam composition of claim 11, wherein said surfactant is selected from the group consisting of a block copolymer, fatty acid ethoxylates, fatty alcohol ethoxylates, polysorbates and glycerol ester ethoxylates.

13. The topical delivery foam composition of claim 11, wherein said surfactant is present in an amount of from about 0.1% to about 10% w/w with respect to the total weight of the composition.

14. The topical delivery foam composition of claim 13, wherein said surfactant is present in an amount of from about 0.1% to about 6% w/w with respect to the total weight of the composition.

15. The topical delivery foam composition of claim 11, wherein said pH adjusting agent is a buffer.

16. The topical delivery foam composition of claim 15, wherein said buffer is selected from the group consisting of citrate/citric acid, acetate/acetic acid, phosphate/phosphoric acid, formate/formic acid, propionate/propionic acid, lactate/lactic acid, carbonate/carbonic acid and ammonium/ammonia buffer.

17. The topical delivery foam composition of claim 16, wherein said buffer is citrate/citric acid.

18. The topical delivery foam composition of claim 11, wherein said aerosol propellant is a hydrocarbon propellant.

19. The topical delivery foam composition of claim 11, wherein the water is present in an amount of about 80% to about 95% w/w with respect to the total weight of the composition.

20. The topical delivery foam composition of claim 11, wherein said composition further comprises xanthan gum.

* * * * *